United States Patent
Lee et al.

(10) Patent No.: US 11,382,676 B2
(45) Date of Patent: Jul. 12, 2022

(54) ARTICULATING IMPLANT CONNECTORS AND RELATED METHODS

(71) Applicant: Medos International Sarl, Le Locle (CH)

(72) Inventors: Kevin Lee, Canton, MA (US); Christopher Ramsay, West Wareham, MA (US); Francisco Amaral, Acushnet, MA (US); Carl Livorsi, Lakeville, MA (US)

(73) Assignee: Medos International Sarl, Le Locle (CH)

( * ) Notice: Subject to any disclaimer, the term of this patent is extended or adjusted under 35 U.S.C. 154(b) by 152 days.

(21) Appl. No.: 16/782,030

(22) Filed: Feb. 4, 2020

(65) Prior Publication Data
US 2020/0170695 A1    Jun. 4, 2020

Related U.S. Application Data

(63) Continuation of application No. 15/471,075, filed on Mar. 28, 2017, now Pat. No. 10,561,454.

(51) Int. Cl.
*A61B 17/70* (2006.01)
*A61B 17/86* (2006.01)

(52) U.S. Cl.
CPC ........ *A61B 17/8615* (2013.01); *A61B 17/705* (2013.01); *A61B 17/7052* (2013.01)

(58) Field of Classification Search
CPC .... A61B 17/6458–6483; A61B 17/7049–7052
See application file for complete search history.

(56) References Cited

U.S. PATENT DOCUMENTS

| | | | |
|---|---|---|---|
| 5,261,909 A | 11/1993 | Sutterlin et al. | |
| 5,312,405 A | 5/1994 | Korotko et al. | |
| 5,569,246 A | 10/1996 | Ojima et al. | |
| 5,613,968 A | 3/1997 | Lin | |
| 5,667,506 A | 9/1997 | Sutterlin | |
| 5,669,910 A * | 9/1997 | Korhonen | A61B 17/7052 606/151 |

(Continued)

FOREIGN PATENT DOCUMENTS

| | | |
|---|---|---|
| CN | 101198284 A | 6/2008 |
| CN | 201194833 Y | 2/2009 |

(Continued)

OTHER PUBLICATIONS

** [No. Author Listed] VuePoint II Technique Guide, 2015, NuVasive®, Inc.; 64 pages.

(Continued)

*Primary Examiner* — Eduardo C Robert
*Assistant Examiner* — Steven J Cotroneo
(74) *Attorney, Agent, or Firm* — Barnes & Thornburg LLP

(57) ABSTRACT

Articulating implant connectors and related methods are disclosed herein. Exemplary connectors can include first and second bodies that are rotatable relative to one another about a rotation axis and selectively lockable to resist or prevent such rotation. Each of the bodies can be configured to couple to a rod or other fixation component, and the connector can be used to lock first and second rods together even when the rods are obliquely angled with respect to one another.

25 Claims, 16 Drawing Sheets

(56) References Cited

U.S. PATENT DOCUMENTS

| | | |
|---|---|---|
| 5,709,685 A | 1/1998 | Dombrowski et al. |
| 5,716,355 A | 2/1998 | Jackson et al. |
| 5,725,528 A | 3/1998 | Errico et al. |
| 5,769,857 A | 6/1998 | Reztzov et al. |
| 5,776,135 A | 7/1998 | Errico et al. |
| 5,876,403 A | 3/1999 | Shitoto |
| 5,885,284 A * | 3/1999 | Errico .............. A61B 17/7052 606/252 |
| 5,980,523 A | 11/1999 | Jackson |
| 6,050,997 A | 4/2000 | Mullane |
| 6,083,226 A | 7/2000 | Fiz |
| 6,096,039 A | 8/2000 | Stoltenberg et al. |
| 6,231,575 B1 | 5/2001 | Krag |
| 6,238,396 B1 | 5/2001 | Lombardo |
| 6,248,104 B1 | 6/2001 | Chopin et al. |
| 6,280,443 B1 | 8/2001 | Gu et al. |
| 6,309,390 B1 | 10/2001 | Le Couedic et al. |
| 6,328,739 B1 | 12/2001 | Liu et al. |
| 6,328,740 B1 | 12/2001 | Richelsoph |
| 6,402,751 B1 | 6/2002 | Hoeck et al. |
| 6,468,276 B1 | 10/2002 | McKay |
| 6,478,798 B1 | 11/2002 | Howland |
| 6,524,310 B1 | 2/2003 | Lombardo et al. |
| 6,551,318 B1 | 4/2003 | Stahurski |
| 6,554,832 B2 | 4/2003 | Shluzas |
| 6,592,585 B2 | 7/2003 | Lee et al. |
| 6,616,668 B2 | 9/2003 | Altarec et al. |
| 6,676,661 B1 | 1/2004 | Martin Benlloch et al. |
| 6,736,775 B2 | 5/2004 | Phillips |
| 6,736,820 B2 | 5/2004 | Biedermann et al. |
| 6,783,526 B1 | 8/2004 | Lin et al. |
| 6,786,907 B2 | 9/2004 | Lange |
| 6,793,657 B2 | 9/2004 | Lee et al. |
| 6,974,460 B2 | 12/2005 | Carbone et al. |
| 7,029,474 B2 | 4/2006 | Richelsoph et al. |
| 7,104,993 B2 | 9/2006 | Baynham et al. |
| 7,122,036 B2 | 10/2006 | Vanacker |
| 7,163,538 B2 | 1/2007 | Altarac et al. |
| 7,166,108 B2 | 1/2007 | Mazda et al. |
| 7,179,261 B2 | 2/2007 | Sicvol et al. |
| 7,189,236 B2 | 3/2007 | Taylor et al. |
| 7,485,132 B1 | 2/2009 | McBride et al. |
| 7,572,277 B2 | 8/2009 | Roussouly et al. |
| 7,575,587 B2 | 8/2009 | Rezach et al. |
| 7,585,314 B2 | 9/2009 | Taylor et al. |
| 7,628,799 B2 | 12/2009 | Richelsoph et al. |
| 7,666,210 B2 | 2/2010 | Franck et al. |
| 7,704,270 B2 | 4/2010 | De Coninck |
| 7,717,938 B2 | 5/2010 | Kim et al. |
| 7,717,940 B2 | 5/2010 | Woods et al. |
| 7,744,632 B2 | 6/2010 | Usher |
| 7,744,634 B2 | 6/2010 | Farris |
| 7,753,940 B2 | 7/2010 | Veldman et al. |
| 7,771,474 B2 | 8/2010 | Cordaro |
| 7,789,897 B2 | 9/2010 | Sanders |
| 7,794,478 B2 | 9/2010 | Nilsson |
| 7,803,174 B2 | 9/2010 | Denis et al. |
| 7,806,912 B2 | 10/2010 | Lawton et al. |
| 7,833,248 B2 | 11/2010 | Markworth et al. |
| 7,837,714 B2 | 11/2010 | Drewry et al. |
| 7,842,071 B2 | 11/2010 | Hawkes |
| 7,901,434 B2 | 3/2011 | Drewry et al. |
| 7,909,854 B2 | 3/2011 | Schwab |
| 7,922,746 B2 | 4/2011 | Miller |
| 7,922,747 B2 | 4/2011 | Kirschman |
| 7,927,355 B2 | 4/2011 | Berrevoets et al. |
| 7,942,901 B2 | 5/2011 | Rezach |
| 7,947,066 B2 | 5/2011 | Tepper et al. |
| 7,959,653 B2 | 6/2011 | Thramann et al. |
| 7,993,371 B2 | 8/2011 | Farris |
| 8,016,862 B2 | 9/2011 | Felix et al. |
| 8,025,679 B2 | 9/2011 | Nichols et al. |
| 8,062,338 B2 | 11/2011 | McBride et al. |
| 8,075,594 B2 | 12/2011 | Purcell |
| 8,080,037 B2 | 12/2011 | Butler et al. |
| 8,097,022 B2 | 1/2012 | Marik |
| 8,109,974 B2 | 2/2012 | Boomer et al. |
| 8,114,133 B2 | 2/2012 | Logan |
| 8,147,519 B2 | 4/2012 | Wilcox |
| 8,152,851 B2 | 4/2012 | Mueller et al. |
| 8,167,908 B2 | 5/2012 | Ely et al. |
| 8,172,879 B2 | 5/2012 | Butler et al. |
| 8,192,467 B2 | 6/2012 | Felix et al. |
| 8,197,515 B2 | 6/2012 | Levy et al. |
| 8,236,028 B2 | 8/2012 | Kalfas et al. |
| 8,241,334 B2 | 8/2012 | Butler et al. |
| 8,246,657 B1 | 8/2012 | Samuel |
| 8,246,665 B2 | 8/2012 | Butler et al. |
| 8,262,700 B2 | 9/2012 | Cho et al. |
| 8,262,701 B2 | 9/2012 | Rathbun et al. |
| 8,292,924 B2 | 10/2012 | Neary et al. |
| 8,298,266 B2 | 10/2012 | Miller |
| 8,298,269 B2 | 10/2012 | Null et al. |
| 8,317,837 B2 | 11/2012 | Rezach et al. |
| 8,337,527 B2 | 12/2012 | Hawkins et al. |
| 8,337,532 B1 | 12/2012 | McLean et al. |
| 8,366,749 B2 | 2/2013 | Sweeney |
| 8,366,750 B2 | 2/2013 | Iott et al. |
| 8,414,616 B2 | 4/2013 | Berrevoets et al. |
| 8,414,617 B2 | 4/2013 | Young et al. |
| 8,419,771 B2 * | 4/2013 | Poirier .............. A61B 17/7052 606/250 |
| 8,419,773 B2 | 4/2013 | Biedermann et al. |
| 8,430,916 B1 | 4/2013 | Winslow et al. |
| 8,460,342 B2 | 6/2013 | Courtney et al. |
| 8,470,001 B2 | 6/2013 | Trautwein et al. |
| 8,591,550 B2 | 11/2013 | Ludwig et al. |
| 8,617,213 B2 | 12/2013 | Moore et al. |
| 8,628,559 B2 | 1/2014 | Iott et al. |
| 8,641,739 B2 | 2/2014 | McLean et al. |
| 8,657,856 B2 | 2/2014 | Gephart et al. |
| 8,668,721 B2 | 3/2014 | Miller |
| 8,715,323 B2 | 5/2014 | Ballard et al. |
| 8,721,689 B2 | 5/2014 | Butler et al. |
| 8,728,124 B2 | 5/2014 | Miller |
| 8,758,411 B1 | 6/2014 | Rayon et al. |
| 8,771,319 B2 | 7/2014 | Prajapati |
| 8,808,332 B2 | 8/2014 | Iott et al. |
| 8,828,056 B2 | 9/2014 | Buss et al. |
| 8,864,798 B2 | 10/2014 | Weiman et al. |
| 8,864,799 B2 | 10/2014 | Kraus |
| 8,870,923 B2 | 10/2014 | Richelsoph |
| 8,882,803 B2 | 11/2014 | Iott et al. |
| 8,888,777 B2 | 11/2014 | Mullaney |
| 8,888,819 B2 | 11/2014 | Frasier et al. |
| 8,920,471 B2 | 12/2014 | Barrus et al. |
| 8,920,475 B1 | 12/2014 | Ziemek et al. |
| 8,945,186 B2 | 2/2015 | Walker et al. |
| 8,951,289 B2 | 2/2015 | Matityahu |
| 8,998,956 B2 | 4/2015 | George et al. |
| 8,998,961 B1 | 4/2015 | Ziemek et al. |
| 9,005,249 B2 | 4/2015 | Rinner et al. |
| 9,023,087 B2 | 5/2015 | Frankel et al. |
| 9,055,980 B2 | 6/2015 | Biedermann |
| 9,060,815 B1 | 6/2015 | Gustine et al. |
| 9,072,547 B2 | 7/2015 | Harper et al. |
| 9,084,630 B2 | 7/2015 | Mullaney |
| 9,095,380 B2 | 8/2015 | Mir et al. |
| 9,101,400 B2 | 8/2015 | Trieu et al. |
| 9,101,405 B2 | 8/2015 | Dickinson et al. |
| 9,107,703 B2 | 8/2015 | Torres |
| 9,113,961 B2 | 8/2015 | Larroque-Lahitette |
| 9,119,675 B2 | 9/2015 | Lee et al. |
| 9,125,691 B2 | 9/2015 | Gunn |
| 9,131,963 B2 | 9/2015 | Predick |
| 9,131,964 B2 | 9/2015 | Blain et al. |
| 9,149,301 B2 | 10/2015 | Asaad et al. |
| 9,155,565 B2 | 10/2015 | Boomer et al. |
| 9,155,580 B2 | 10/2015 | Cormier et al. |
| 9,186,184 B2 | 11/2015 | Janowski |
| 9,198,696 B1 | 12/2015 | Bannigan et al. |
| 9,204,901 B2 | 12/2015 | Black et al. |
| 9,220,541 B1 | 12/2015 | Dant et al. |
| 9,247,964 B1 | 2/2016 | Shoshtaev |

(56) References Cited

U.S. PATENT DOCUMENTS

| | | |
|---|---|---|
| 9,265,548 B2 | 2/2016 | Jones et al. |
| 9,271,763 B2 | 3/2016 | Barrus et al. |
| 9,339,307 B2 | 5/2016 | McClintock et al. |
| 9,345,521 B2 | 5/2016 | Ziolo |
| 9,421,041 B2 | 8/2016 | Richelsoph |
| 9,433,445 B2 | 9/2016 | Ramsay et al. |
| 9,451,994 B1* | 9/2016 | Whipple ............ A61B 17/7043 |
| 9,474,554 B2 | 10/2016 | Strnad |
| 9,517,089 B1 | 12/2016 | Casey et al. |
| 9,561,058 B2 | 2/2017 | Lange et al. |
| 9,579,126 B2 | 2/2017 | Zhang et al. |
| 9,615,867 B2 | 4/2017 | Picetti et al. |
| 9,629,663 B2 | 4/2017 | Ludwig et al. |
| 9,649,136 B2 | 5/2017 | George et al. |
| 9,693,808 B2 | 7/2017 | Fauth et al. |
| 9,724,131 B2 | 8/2017 | Bootwala et al. |
| 9,770,269 B1 | 9/2017 | Shoshtaev |
| 9,956,009 B1 | 5/2018 | Shoshtaev |
| 10,238,432 B2 | 3/2019 | Carruth et al. |
| 10,321,939 B2 | 6/2019 | Lee et al. |
| 10,398,476 B2 | 9/2019 | Lee et al. |
| 10,492,835 B2 | 12/2019 | Lee et al. |
| 10,517,647 B2 | 12/2019 | Lee et al. |
| 10,561,454 B2 | 2/2020 | Lee et al. |
| 10,869,695 B2 | 12/2020 | Carruth et al. |
| 10,966,761 B2 | 4/2021 | Lee et al. |
| 11,058,463 B2 | 7/2021 | Lee et al. |
| 11,076,890 B2 | 8/2021 | Ortiz et al. |
| 11,160,583 B2 | 11/2021 | Lee et al. |
| 2002/0042614 A1* | 4/2002 | Ueyama ............ A61B 17/7002 606/261 |
| 2003/0045878 A1 | 3/2003 | Petit et al. |
| 2003/0045879 A1 | 3/2003 | Minfelde et al. |
| 2003/0153914 A1 | 8/2003 | Oribe et al. |
| 2004/0111088 A1 | 6/2004 | Picetti et al. |
| 2004/0147929 A1 | 7/2004 | Biedermann et al. |
| 2004/0162558 A1 | 8/2004 | Hegde et al. |
| 2005/0131404 A1 | 6/2005 | Mazda et al. |
| 2005/0149019 A1 | 7/2005 | Sasing et al. |
| 2005/0171537 A1 | 8/2005 | Mazel et al. |
| 2005/0228326 A1 | 10/2005 | Kalfas et al. |
| 2005/0228377 A1 | 10/2005 | Chao et al. |
| 2005/0228378 A1* | 10/2005 | Kalfas ................ A61B 17/705 606/252 |
| 2005/0228382 A1 | 10/2005 | Richelsoph et al. |
| 2006/0039750 A1 | 2/2006 | Thomke et al. |
| 2006/0058789 A1 | 3/2006 | Kim et al. |
| 2006/0064090 A1 | 3/2006 | Park |
| 2006/0064091 A1 | 3/2006 | Ludwig et al. |
| 2006/0079892 A1 | 4/2006 | Roychowdhury et al. |
| 2006/0177263 A1* | 8/2006 | Thomke ............ F16B 7/0433 403/322.4 |
| 2006/0206114 A1 | 9/2006 | Ensign et al. |
| 2006/0229611 A1 | 10/2006 | Avery et al. |
| 2006/0241598 A1 | 10/2006 | Khalili |
| 2006/0282074 A1 | 12/2006 | Renaud et al. |
| 2007/0049932 A1 | 3/2007 | Richelsoph et al. |
| 2007/0100339 A1 | 5/2007 | Clement et al. |
| 2007/0123860 A1 | 5/2007 | Francis et al. |
| 2007/0173825 A1 | 7/2007 | Sharifi-Mehr et al. |
| 2007/0173829 A1 | 7/2007 | Drewry et al. |
| 2007/0233062 A1 | 10/2007 | Berry |
| 2007/0233090 A1 | 10/2007 | Naifeh et al. |
| 2007/0250061 A1 | 10/2007 | Chin et al. |
| 2007/0270805 A1 | 11/2007 | Miller et al. |
| 2007/0270817 A1 | 11/2007 | Rezach |
| 2007/0270818 A1 | 11/2007 | Rezach |
| 2007/0276384 A1 | 11/2007 | Spratt |
| 2008/0021466 A1 | 1/2008 | Shadduck et al. |
| 2008/0045963 A1 | 2/2008 | Abdou |
| 2008/0058805 A1 | 3/2008 | Stuart |
| 2008/0082112 A1 | 4/2008 | Lawton et al. |
| 2008/0109039 A1 | 5/2008 | Michielli et al. |
| 2008/0177318 A1 | 7/2008 | Veldman et al. |
| 2008/0177323 A1 | 7/2008 | Null et al. |
| 2008/0234743 A1 | 9/2008 | Marik |
| 2008/0255617 A1 | 10/2008 | Cho et al. |
| 2008/0262552 A1 | 10/2008 | Kim |
| 2008/0262553 A1* | 10/2008 | Hawkins ............ A61B 17/705 606/278 |
| 2008/0269810 A1 | 10/2008 | Zhang et al. |
| 2008/0281361 A1 | 11/2008 | Vittur et al. |
| 2009/0036929 A1 | 2/2009 | Regies et al. |
| 2009/0082812 A1 | 3/2009 | Lewis |
| 2009/0105765 A1 | 4/2009 | Strnad |
| 2009/0157120 A1 | 6/2009 | Marino et al. |
| 2009/0163956 A1 | 6/2009 | Biedermann et al. |
| 2009/0187217 A1 | 7/2009 | Weiman et al. |
| 2009/0204153 A1 | 8/2009 | Suzuki et al. |
| 2009/0222042 A1 | 9/2009 | Firkins et al. |
| 2009/0228046 A1 | 9/2009 | Garamszegi |
| 2009/0249851 A1 | 10/2009 | Isaacs |
| 2010/0004686 A1 | 1/2010 | Lemoine |
| 2010/0004693 A1 | 1/2010 | Miller et al. |
| 2010/0010545 A1 | 1/2010 | Park et al. |
| 2010/0087864 A1 | 4/2010 | Klein et al. |
| 2010/0087867 A1 | 4/2010 | Klein et al. |
| 2010/0094345 A1 | 4/2010 | Saidha et al. |
| 2010/0094346 A1 | 4/2010 | Matityahu |
| 2010/0094349 A1 | 4/2010 | Hammer et al. |
| 2010/0114165 A1 | 5/2010 | Ely |
| 2010/0114167 A1 | 5/2010 | Wilcox et al. |
| 2010/0160981 A1 | 6/2010 | Butler et al. |
| 2010/0204733 A1 | 8/2010 | Rathbun et al. |
| 2010/0241171 A1 | 9/2010 | Clement et al. |
| 2010/0274286 A1 | 10/2010 | Blain et al. |
| 2010/0280552 A1 | 11/2010 | Lee |
| 2010/0298884 A1 | 11/2010 | Faizan et al. |
| 2010/0324599 A1 | 12/2010 | Montello et al. |
| 2011/0034957 A1 | 2/2011 | Biedermann |
| 2011/0046675 A1 | 2/2011 | Barrus et al. |
| 2011/0066187 A1 | 3/2011 | Fang et al. |
| 2011/0087287 A1 | 4/2011 | Reeder, Jr. et al. |
| 2011/0087288 A1 | 4/2011 | Stevenson et al. |
| 2011/0098748 A1 | 4/2011 | Jangra |
| 2011/0106178 A1 | 5/2011 | Schwab |
| 2011/0112533 A1* | 5/2011 | Venturini ............ F16B 7/0493 606/54 |
| 2011/0112580 A1 | 5/2011 | Clement et al. |
| 2011/0137345 A1 | 6/2011 | Stoll et al. |
| 2011/0152936 A1 | 6/2011 | Gil et al. |
| 2011/0196425 A1 | 8/2011 | Rezach et al. |
| 2011/0245872 A1 | 10/2011 | Nilsson |
| 2011/0245878 A1 | 10/2011 | Franks et al. |
| 2011/0307018 A1 | 12/2011 | Zucherman et al. |
| 2012/0029571 A1* | 2/2012 | Schwab ............ A61B 17/705 606/278 |
| 2012/0059421 A1 | 3/2012 | Aferzon |
| 2012/0071926 A1 | 3/2012 | Jani et al. |
| 2012/0083845 A1 | 4/2012 | Winslow et al. |
| 2012/0095512 A1 | 4/2012 | Nihalani |
| 2012/0130436 A1 | 5/2012 | Haskins et al. |
| 2012/0158064 A1 | 6/2012 | Kroll |
| 2012/0203278 A1 | 8/2012 | Gil et al. |
| 2012/0221053 A1 | 8/2012 | Copf |
| 2012/0226316 A1 | 9/2012 | Dant et al. |
| 2012/0232593 A1 | 9/2012 | Predick |
| 2012/0259369 A1 | 10/2012 | Hammer |
| 2012/0290013 A1 | 11/2012 | Simonson |
| 2012/0296335 A1 | 11/2012 | Mullaney |
| 2012/0303062 A1 | 11/2012 | Amstutz et al. |
| 2013/0018422 A1* | 1/2013 | Rinner ............ A61B 17/7049 606/278 |
| 2013/0030468 A1 | 1/2013 | Le Couedic et al. |
| 2013/0079826 A1 | 3/2013 | Simonson |
| 2013/0085534 A1 | 4/2013 | Hainard et al. |
| 2013/0096617 A1 | 4/2013 | Ballard et al. |
| 2013/0123854 A1* | 5/2013 | Kondrashov ...... A61B 17/7038 606/264 |
| 2013/0211457 A1 | 8/2013 | Dickinson et al. |
| 2013/0253588 A1 | 9/2013 | Traynelis et al. |
| 2013/0268004 A1 | 10/2013 | Rathbun |
| 2013/0274807 A1 | 10/2013 | Prajapati |
| 2013/0274808 A1 | 10/2013 | Larroque-Lahitette et al. |

(56) References Cited

U.S. PATENT DOCUMENTS

| | | |
|---|---|---|
| 2014/0018858 A1 | 1/2014 | Laeng et al. |
| 2014/0066990 A1 | 3/2014 | Akbarnia et al. |
| 2014/0088650 A1 | 3/2014 | Taddia et al. |
| 2014/0114359 A1 | 4/2014 | Hawkes |
| 2014/0135839 A1 | 5/2014 | Frankel et al. |
| 2014/0148856 A1 | 5/2014 | Ibarra et al. |
| 2014/0222076 A1 | 8/2014 | Jackson |
| 2014/0249581 A1 | 9/2014 | Stachniak |
| 2014/0277146 A1 | 9/2014 | Li et al. |
| 2014/0277160 A1* | 9/2014 | Ziolo ............... A61B 17/7049 606/278 |
| 2014/0277163 A1 | 9/2014 | Kretzer et al. |
| 2014/0303674 A1 | 10/2014 | Sasing |
| 2014/0316468 A1 | 10/2014 | Keiser et al. |
| 2014/0336706 A1 | 11/2014 | Garamszegi |
| 2014/0343613 A1 | 11/2014 | Eliasen et al. |
| 2015/0032160 A1 | 1/2015 | Carbone et al. |
| 2015/0057707 A1 | 2/2015 | Barrus et al. |
| 2015/0057708 A1 | 2/2015 | Ballard et al. |
| 2015/0073479 A1 | 3/2015 | Rinner |
| 2015/0094769 A1 | 4/2015 | Abbasi |
| 2015/0119941 A1 | 4/2015 | Daniels et al. |
| 2015/0190178 A1 | 7/2015 | McCarthy et al. |
| 2015/0196328 A1 | 7/2015 | Hirschl et al. |
| 2015/0223844 A1 | 8/2015 | Leff et al. |
| 2015/0230830 A1 | 8/2015 | Frankel et al. |
| 2015/0282842 A1 | 10/2015 | Beyar et al. |
| 2015/0313645 A1 | 11/2015 | Hansell |
| 2015/0359568 A1 | 12/2015 | Rezach |
| 2016/0135846 A1 | 5/2016 | Mirda |
| 2016/0143665 A1 | 5/2016 | Biedermann et al. |
| 2016/0166289 A1 | 6/2016 | Alsup et al. |
| 2016/0287294 A1 | 10/2016 | Kubo et al. |
| 2017/0020578 A1 | 1/2017 | Mosnier et al. |
| 2017/0079690 A1 | 3/2017 | Oberlander et al. |
| 2017/0086885 A1 | 3/2017 | Duncan et al. |
| 2017/0086895 A1 | 3/2017 | Barra et al. |
| 2017/0095271 A1 | 4/2017 | Faulhaber |
| 2017/0105764 A1 | 4/2017 | Williams |
| 2017/0112540 A1 | 4/2017 | Montello et al. |
| 2017/0119439 A1 | 5/2017 | Ozdil et al. |
| 2017/0128105 A1 | 5/2017 | Patrinicola et al. |
| 2017/0128107 A1 | 5/2017 | Alsup et al. |
| 2017/0209182 A1 | 7/2017 | Picetti et al. |
| 2017/0245900 A1 | 8/2017 | Rezach |
| 2017/0281247 A1 | 10/2017 | Murray et al. |
| 2017/0311985 A1 | 11/2017 | Bobbitt et al. |
| 2017/0333087 A1 | 11/2017 | Lee et al. |
| 2017/0333088 A1 | 11/2017 | Lee et al. |
| 2017/0348026 A1 | 12/2017 | Stein et al. |
| 2018/0042647 A1 | 2/2018 | Cowan et al. |
| 2018/0098798 A1 | 4/2018 | Italiaie et al. |
| 2018/0116695 A1 | 5/2018 | Armstrong et al. |
| 2018/0161073 A1 | 6/2018 | Lee et al. |
| 2018/0168694 A1 | 6/2018 | Lee et al. |
| 2018/0195150 A1 | 7/2018 | Meyer et al. |
| 2018/0206890 A1 | 7/2018 | Rezach |
| 2018/0228516 A1 | 8/2018 | Armstrong et al. |
| 2018/0228518 A1 | 8/2018 | Carruth et al. |
| 2018/0243009 A1 | 8/2018 | Bobbitt et al. |
| 2018/0280062 A1 | 10/2018 | Lee et al. |
| 2018/0280063 A1 | 10/2018 | Lee et al. |
| 2018/0317972 A1 | 11/2018 | Abbasi |
| 2019/0167313 A1 | 6/2019 | Ortiz et al. |
| 2019/0175226 A1 | 6/2019 | Carruth et al. |
| 2019/0183541 A1 | 6/2019 | Lee et al. |
| 2019/0269440 A1 | 9/2019 | Patrinicola et al. |
| 2019/0336178 A1 | 11/2019 | Finn et al. |
| 2019/0365432 A1 | 12/2019 | Lee et al. |
| 2020/0060729 A1 | 2/2020 | Lee et al. |
| 2020/0069341 A1 | 3/2020 | Abbasi |
| 2020/0085473 A1 | 3/2020 | Lee et al. |
| 2021/0068872 A1 | 3/2021 | Carruth et al. |
| 2021/0186572 A1 | 6/2021 | Lee et al. |

FOREIGN PATENT DOCUMENTS

| | | |
|---|---|---|
| EP | 1857064 A1 | 11/2007 |
| EP | 2 319 436 A1 | 5/2011 |
| EP | 2730242 A1 | 5/2014 |
| JP | H09-503148 A | 3/1997 |
| JP | 2001-517122 A | 10/2001 |
| JP | 2003-515380 A | 5/2003 |
| JP | 2008-523890 A | 7/2008 |
| JP | 2009-533087 A | 9/2009 |
| JP | 2010-506670 A | 3/2010 |
| JP | 2014-521383 A | 8/2014 |
| JP | 2016-501690 A | 1/2016 |
| KR | 20100054713 A | 5/2010 |
| WO | 2005/044119 A2 | 5/2005 |
| WO | 2007/124242 A1 | 11/2007 |
| WO | 2009/110865 A8 | 12/2009 |
| WO | 2011/004222 A1 | 1/2011 |
| WO | 2011/006155 A1 | 1/2011 |
| WO | 2015/017250 A1 | 2/2015 |

OTHER PUBLICATIONS

**Akbarnia, B., et al., "Pediatric Isola® Prebent Rod Placement," (Technique Manual), DePuy Acromed, Oct. 2010; 2 pages.
**International Search Report and Written Opinion for Application No. PCT/US2017/031883, dated Aug. 2, 2017. (15 pgs).
International Search Report and Written Opinion for Application No. PCT/US2018/017034, dated Aug. 1, 2018 (20 pages).
**International Search Report and Written Opinion for Application No. PCT/US2018/024731, dated Jul. 2, 2018 (17 pages).
**International Search Report and Written Opinion for Application No. PCT/US2018/062786, dated Feb. 4, 2019 (4 pages).
**Invitation to Pay Additional Fees for Application No. PCT/US2018/017034, dated May 18, 2018 (18 pages).
Chinese Office Action for Application No. 201780030641.3, dated Nov. 1, 2021 (15 pages).
Japanese Office Action for Application No. 2018-560664, dated Apr. 21, 2021 (6 pages) Translation Only.
Japanese Office Action for Application No. 2019-543334, dated Oct. 27, 2021 (15 pages).

* cited by examiner

FIG. 3C

ARTICULATING IMPLANT CONNECTORS AND RELATED METHODS

RELATED APPLICATION

The present application is a continuation of U.S. application Ser. No. 15/471,075, filed Mar. 28, 2017, which is incorporated herein by reference in its entirety.

FIELD

Articulating implant connectors and related methods are disclosed herein.

BACKGROUND

Fixation systems can be used in orthopedic surgery to maintain a desired spatial relationship between multiple bones or bone fragments. For example, various conditions of the spine, such as fractures, deformities, and degenerative disorders, can be treated by attaching a spinal fixation system to one or more vertebrae. Such systems typically include a spinal fixation element, such as a rigid or flexible rod or plate, that is coupled to the vertebrae by attaching the element to various anchoring devices, such as screws, hooks, or wires. Once installed, the fixation system holds the vertebrae in a desired position until healing or spinal fusion can occur, or for some other period of time.

There are many instances in which it may be desirable to connect multiple implants to each other. For example, some revision surgeries involve extending a previously-installed construct to additional vertebral levels by coupling a newly-installed spinal rod to a previously-installed rod. By way of further example, aspects of the patient's anatomy, the surgical technique used, or the desired correction may require that multiple spinal rods be connected to one another. As yet another example, coupling multiple rods to one another can improve the overall strength and stability of an implanted construct.

There can be various difficulties associated with connecting multiple implants to each other. The available space for the implanted construct can often be very limited, particularly in the cervical area of the spine. Also, aligning and positioning implants and connectors in the surgical wound may be challenging or cumbersome for the surgeon. There is a continual need for improved implant connectors and related methods.

SUMMARY

Articulating implant connectors and related methods are disclosed herein. Exemplary connectors can include first and second bodies that are rotatable relative to one another about a rotation axis and selectively lockable to resist or prevent such rotation. Each of the bodies can be configured to couple to a rod or other fixation component, and the connector can be used to lock first and second rods together even when the rods are obliquely angled with respect to one another.

In some embodiments, a connector can include a first body that defines a first rod-receiving recess, the first body having proximal and distal ends that define a proximal-distal axis extending therebetween; a second body that defines a second rod-receiving recess, the second body having proximal and distal ends that define a proximal-distal axis extending therebetween; a hinge pin that couples the first body to the second body, a central longitudinal axis of the hinge pin defining a rotation axis about which the first and second bodies rotate relative to one another; and a fastener movable with respect to at least one of the first and second bodies to urge the first and second bodies towards one another along the rotation axis and thereby lock relative rotation of the first and second bodies about the rotation axis.

The fastener can secure a rod to one of the first and second rod-receiving recesses. The fastener can be a first fastener configured to secure a first rod within the first rod-receiving recess. The connector can include a second fastener configured to secure a second rod in the second rod-receiving recess. The hinge pin can be formed integrally with the first body. The hinge pin can be rotatable relative to both of the first and second bodies. The first and second bodies can include respective bearing surfaces configured to bear against one another to lock relative rotation of the first and second bodies about the rotation axis. The bearing surfaces can be defined by complementary male and female structures of the first and second bodies. The first body can include a conical male projection, an outer surface of which defines the bearing surface of the first body. The second body can include a conical female recess, an inner surface of which defines the bearing surface of the second body. The bearing surfaces can each include teeth or splines. The hinge pin can be received within a cavity formed in the first body or the second body. The hinge pin can translate longitudinally within the cavity as the fastener is moved relative to said at least one of the first and second bodies. The proximal-distal axes of the first and second bodies can be obliquely angled with respect to one another. A force applied by the fastener can be transferred to the hinge pin through a saddle. The saddle can include a conical surface that engages and bears against a corresponding conical surface of the hinge pin to pull the first and second bodies towards one another. The saddle can include a keel extending distally therefrom. The keel can be received within a slot formed in the hinge pin. The keel can have a bearing surface that engages and bears against a corresponding bearing surface of the slot to pull the first and second bodies towards one another. The bearing surfaces of the keel and the slot can lie in planes that are obliquely angled with respect to the rotation axis. The saddle can include first and second keels defining a space therebetween in which a central rib of the hinge pin is received. The first and second keels can have bearing surfaces that engage and bear against corresponding bearing surface of the hinge pin. The hinge pin can include a rod seat formed therein. The rod seat can be configured such that urging a rod against the rod seat causes the hinge pin to translate relative to at least one of the first and second bodies along the rotation axis. The rod seat can be positioned relative to the first rod-receiving recess such that a lateral sidewall of the rod seat interferes with a rod as the rod is seated in the first rod-receiving recess. The rod seat can be curved in multiple planes.

In some embodiments, a connector can include a first body that defines a first rod-receiving recess; a hinge pin formed integrally with the first body and extending laterally therefrom to a free end; a second body that defines a second rod-receiving recess, the second body having a cavity in which the free end of the hinge pin is received to couple the second body to the first body such that the first and second bodies rotate relative to one another about a rotation axis; a first fastener configured to secure a first rod within the first rod-receiving recess; and a second fastener configured to secure a second rod within the second rod-receiving recess and to urge the first and second bodies towards one another along the rotation axis to lock relative rotation of the first and second bodies about the rotation axis.

The second fastener can be configured to bear against a saddle disposed within the second rod-receiving recess to urge a bearing surface of the saddle against a bearing surface of the hinge pin to move the first and second bodies towards one another. The second fastener can be configured to bear against a rod disposed within the second rod-receiving recess to urge the rod against a rod seat of the hinge pin to move the first and second bodies towards one another.

In some embodiments, a surgical method can include inserting a first rod into a first rod-receiving recess of a first body of a connector; inserting a second rod into a second rod-receiving recess of a second body of the connector, the second body being coupled to the first body by a hinge pin; rotating the first body relative to the second body about a rotation axis defined by the hinge pin; moving a fastener with respect to at least one of the first and second bodies to urge the first and second bodies towards one another along the rotation axis and thereby lock relative rotation of the first and second bodies about the rotation axis; and securing the first and second rods to an anatomy of a patient.

The first rod can be secured to a cervical spine of the patient by one or more bone anchors and the second rod can be secured to a thoracic spine of the patient by one or more bone anchors. Rotating the first body relative to the second body can cause the first and second rods to be obliquely angled with respect to one another. Moving the fastener can be effective both to secure one of the first and second rods to the connector and to lock rotation of the connector.

BRIEF DESCRIPTION OF THE DRAWINGS

FIG. 3C is a sectional side view of the connector and rods of FIG. 3A;

DETAILED DESCRIPTION

Figure 1A:
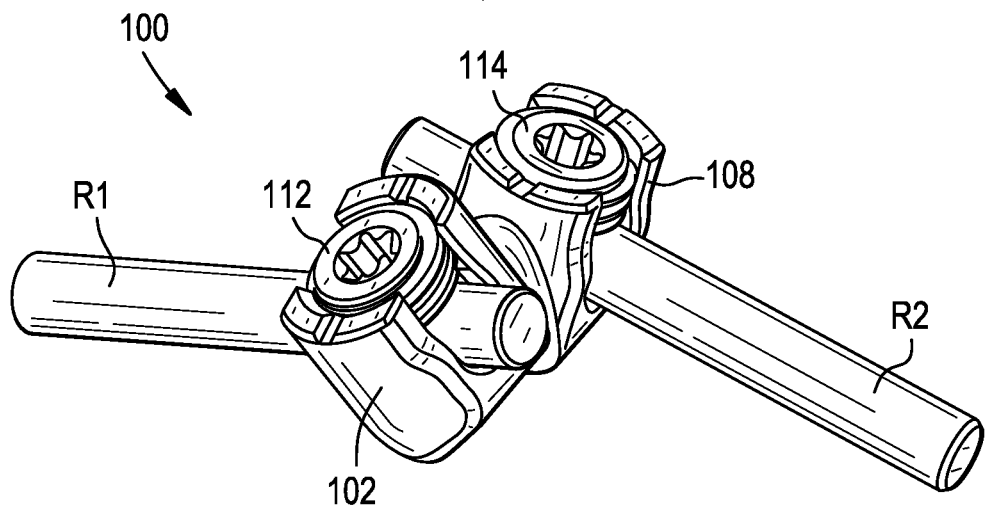
FIG. 1A is a perspective view of a connector, shown with first and second rods.
Figure 1B:
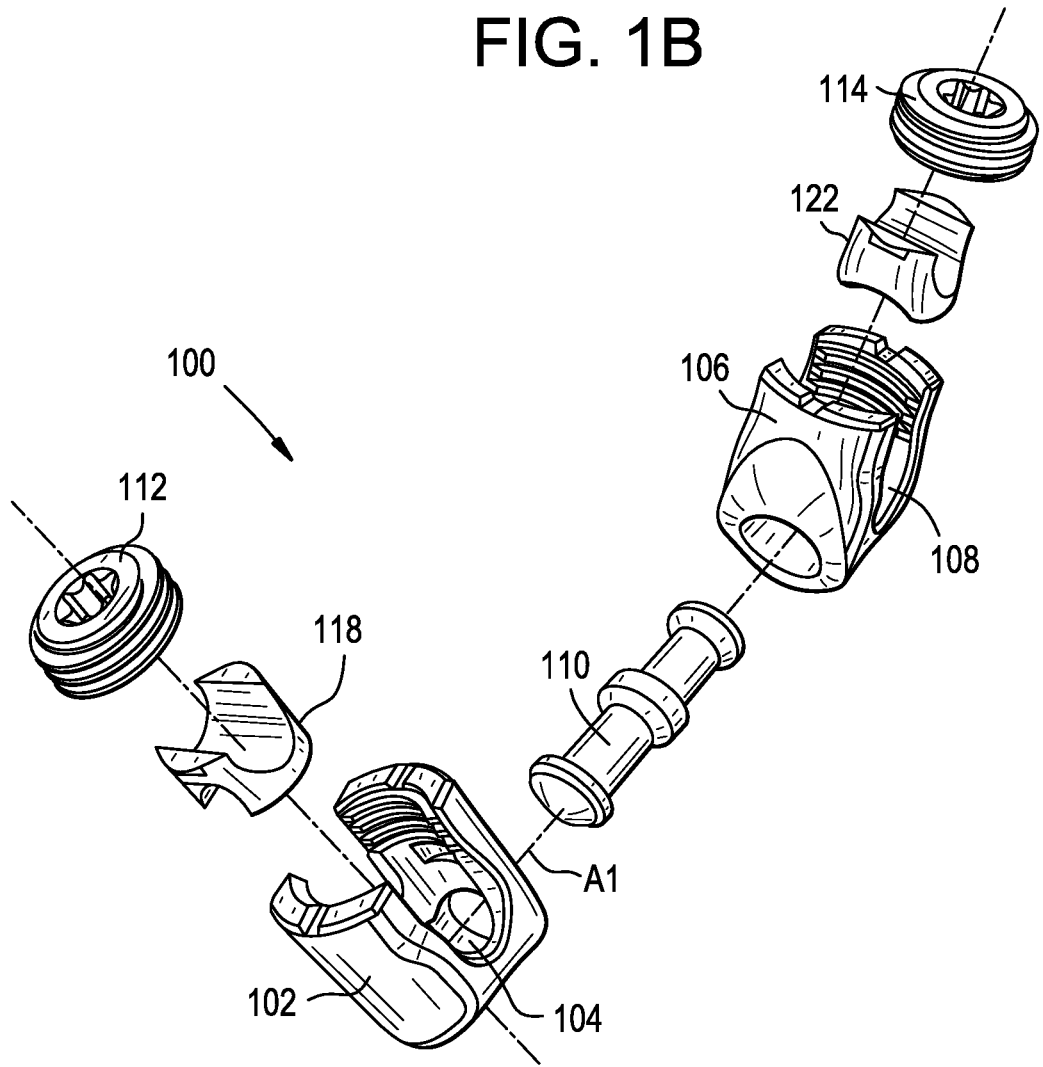
FIG. 1B is an exploded perspective view of the connector of FIG. 1A.

Articulating implant connectors and related methods are disclosed herein. Exemplary connectors can include first and second bodies that are rotatable relative to one another about a rotation axis and selectively lockable to resist or prevent such rotation. Each of the bodies can be configured to couple to a rod or other fixation component, and the connector can be used to lock first and second rods together even when the rods are obliquely angled with respect to one another.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

FIGS. 1A-1L illustrate an exemplary embodiment of a connector 100. As shown, the connector 100 can include a first body 102 that defines a first rod-receiving recess or channel 104 and a second body 106 that defines a second rod-receiving recess or channel 108. The first and second bodies 102, 106 can be connected to one another at least in part by a hinge pin 110. The hinge pin 110 can define a rotation axis A1 about which the first and second bodies 102, 106 can rotate relative to one another. The connector 100 can include first and second fasteners 112, 114 configured to secure respective first and second rods R1, R2 or other fixation elements to the connector 100.

At least one of the fasteners 112, 114 can further be configured to urge the first and second bodies 102, 106 towards one another and thereby lock relative rotation of the first and second bodies about the rotation axis A1. For example, the first fastener 112 can be tightened to secure a first rod R1 within the first body 102 and to apply a force to a first ramped, curved, or otherwise tapered surface 116 of the hinge pin 110 to draw the first and second bodies 102, 106 towards one another, locking rotation therebetween. In the illustrated embodiment, a force applied by the first fastener 112 is transferred to the hinge pin 110 through the first rod R1 and through a first saddle 118 disposed between the first rod and the hinge pin. In other arrangements, the saddle 118 can be omitted and the first rod R1 can bear directly against the hinge pin 110. In still further arrangements, the first fastener 112 can bear directly against the saddle 118. For example, the first fastener 112 can include an outer set screw that bears against the saddle 118 to lock relative rotation of the bodies 102, 106, and an inner set screw that bears against the first rod R1 to secure the first rod to the connector 100.

Similarly, the second fastener 114 can be tightened to secure a second rod R2 within the second body 106 and to apply a force to a second ramped, curved, or otherwise tapered surface 120 of the hinge pin 110 to draw the first and second bodies 102, 106 towards one another, locking rotation therebetween. In the illustrated embodiment, a force applied by the second fastener 114 is transferred to the hinge pin 110 through the second rod R2 and through a second saddle 122 disposed between the second rod and the hinge pin. In other arrangements, the saddle 122 can be omitted and the second rod R2 can bear directly against the hinge pin 110. In still further arrangements, the second fastener 114 can bear directly against the saddle 122. For example, the second fastener 114 can include an outer set screw that bears against the saddle 122 to lock relative rotation of the bodies 102, 106, and an inner set screw that bears against the second rod R2 to secure the second rod to the connector 100.

The geometries of the various components of the connector 100 can be configured such that tightening either of the fasteners 112, 114 individually is effective to lock relative rotation between the bodies 102, 106, or such that both fasteners 112, 114 must be tightened before relative rotation between the bodies 102, 106 is locked.

The ability to rotate the first and second bodies 102, 106 relative to one another about the rotation axis A1 can advantageously allow first and second rods R1, R2 to be locked together even when the rods are obliquely angled with respect to one another, e.g., in the sagittal plane or in the coronal plane. The connector 100 can be particularly useful in connecting tandem rods of a spinal fixation construct across the cervical-thoracic (CT) junction of a patient. For example, the connector 100 can secure the rods R1, R2 in a laterally-offset arrangement to accommodate the different screw trajectories that may occur at the CT junction. By way of further example, the ability of the connector 100 to articulate can allow a cervical rod and a thoracic rod to be locked to one another at an oblique angle in the sagittal plane, e.g., to restore natural lordosis or kyphosis. The connector 100 can also be particularly useful in spinal deformity correction and other procedures in which multiple angled rods are to be coupled to one another.

Figure 1C:
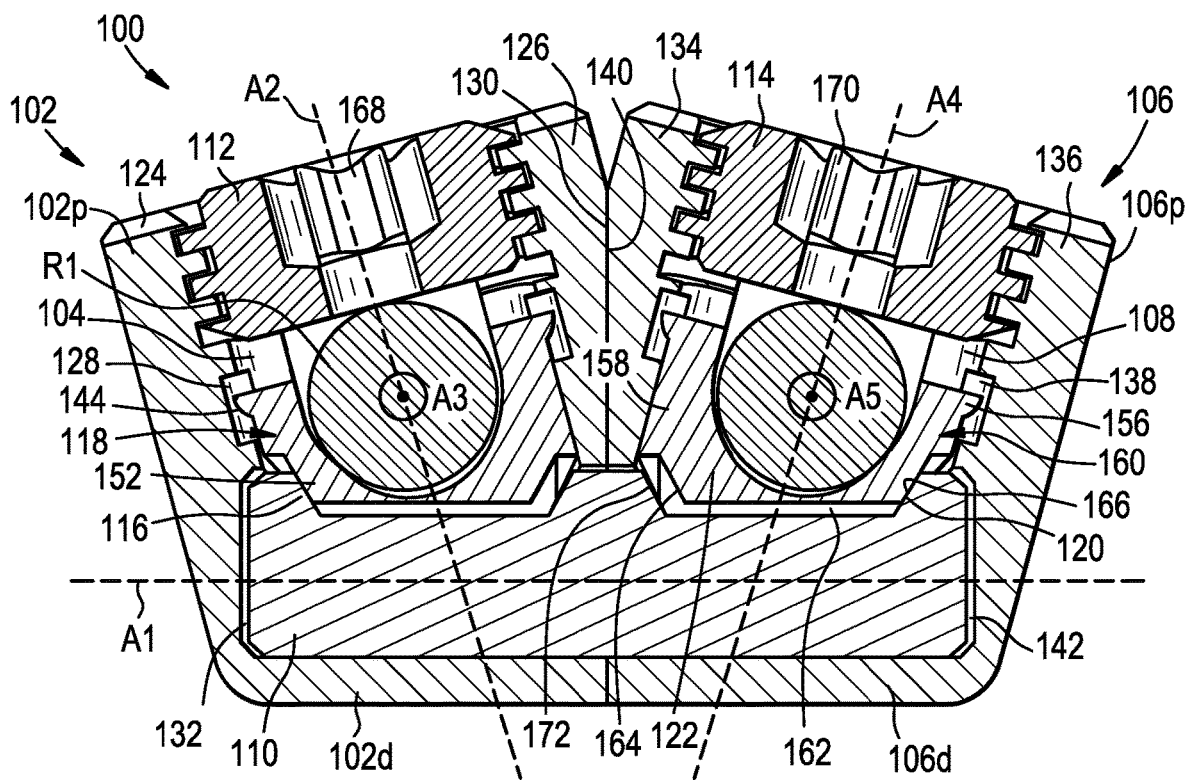
FIG. 1C is a sectional side view of the connector and rods of FIG. 1A.
Figure 1D:
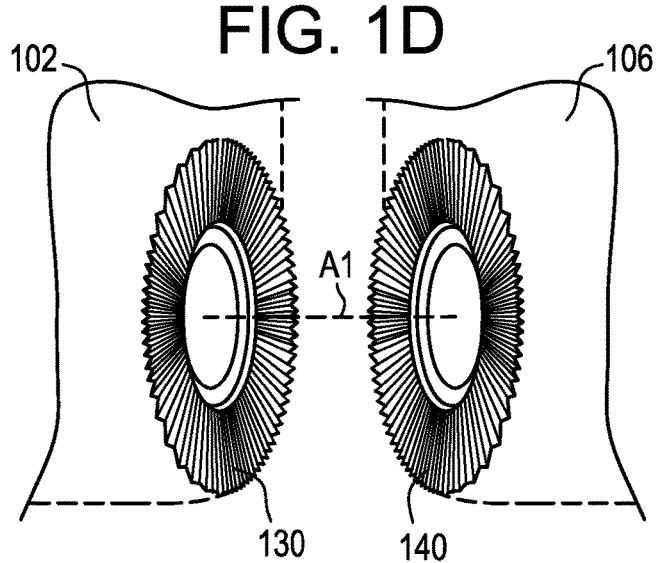
FIG. 1D is a partial exploded view of the connector of FIG. 1A.
Figure 1E:
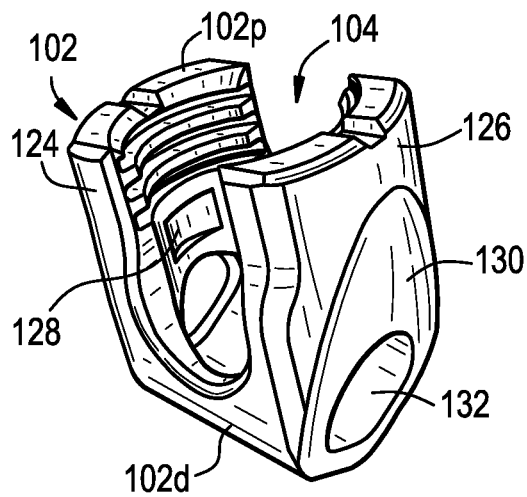
FIG. 1E is a perspective view of a first body of the connector of FIG. 1A.
Figure 1F:
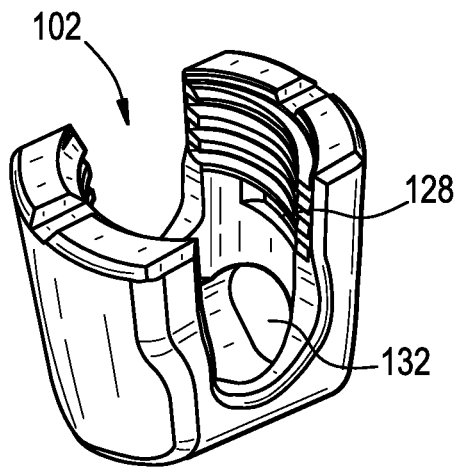
FIG. 1F is another perspective view of the first body of FIG. 1E.

The first body 102 is shown in greater detail in FIGS. 1C, 1E, and 1F. The first body 102 can include proximal and distal ends 102p, 102d that define a proximal-distal axis A2. The proximal end 102p of the body 102 can include a pair of spaced apart arms 124, 126 that define the first rod-receiving recess 104 therebetween. A rod R1 disposed in the first rod-receiving recess 104 can have a central longitudinal rod axis A3. The first rod-receiving recess 104 can be open in a proximal direction, such that a rod R1 can be inserted into the recess by moving the rod distally with respect to the connector 100. Alternatively, the first rod-receiving recess 104 can be open in distal direction, open in a lateral direction, or closed such that the rod R1 must be translated along the axis A3 to insert the rod into the recess 104.

Each of the arms 124, 126 can extend from the distal portion 102d of the body 102 to a free end. The outer surfaces of each of the arms 124, 126 can include a feature (not shown), such as a recess, dimple, notch, projection, or the like, to facilitate coupling of the connector 100 to various instruments. For example, the outer surface of each arm 124, 126 can include an arcuate groove at the respective free end of the arms for attaching the connector 100 to an extension tower or retractor. The arms 124, 126 can include or can be coupled to extension or reduction tabs (not shown) that extend proximally from the body 102 to functionally extend the length of the arms 124, 126. The extension tabs can facilitate insertion and reduction of a rod or other implant, as well as insertion and locking of the first fastener 112. The extension tabs can be configured to break away or otherwise be separated from the arms 124, 126.

The inner surfaces of each of the arms 124, 126 can be configured to mate with the first fastener 112. For example, the inner surfaces of the arms 124, 126 can include threads that correspond to external threads formed on the first fastener 112. Accordingly, rotation of the first fastener 112 with respect to the body 102 about the axis A2 can be effective to translate the first fastener with respect to the body axially along the axis A2.

The inner surfaces of each of the arms 124, 126 can include features for retaining the first saddle 118 within the first body 102 and/or for limiting or preventing certain movement of the saddle with respect to the body. For example, the arms 124, 126 can each include a recess 128 configured to receive a corresponding projection 144 formed on the saddle 118. Each recess 128 can define a distal-facing upper surface configured to limit proximal travel of the saddle 118 along the axis A2 and a proximal-facing lower surface configured to limit distal travel of the saddle 118 along the axis A2. The recess 128 can extend through less than an entire width of the arm in which the recess is formed, such that rotation of the saddle 118 relative to the body 102 about the axis A2 is limited or prevented when the projections 144 of the saddle are received within the recesses.

It will be appreciated that the illustrated retention features are exemplary, and that various other retention features can be used instead or in addition. For example, the structures can be reversed such that the body 102 includes projections received within corresponding recesses formed in the saddle 118. As another example, the saddle 118 and the body 102 can include opposed grooves in which a snap ring or C-clip is received to retain the saddle to the body. As yet another example, the saddle 118 and the hinge pin 110 can include opposed grooves in which a snap ring or C-clip is received to retain the saddle to the hinge pin.

The first body 102 can include an outer bearing surface 130 configured to contact and bear against a corresponding bearing surface 140 of the second body 106. The respective bearing surfaces 130, 140 of the bodies 102, 106 can bear against one another to lock relative rotation between the bodies as they are urged towards one another. In the illustrated embodiment, the bearing surfaces 130, 140 of the first and second bodies 102, 106 are opposed planar surfaces configured to frictionally-engage one another when the connector 100 is locked. It will be appreciated, however, that various other arrangements can be used instead or in addition. For example, the bearing surfaces 130, 140 can include or can be defined by complementary male and female structures of the first and second bodies 102, 106. In some embodiments, the first body 102 can include a conical male projection, an outer surface of which defines the bearing surface 130 of the first body, and the second body 106 can include a conical female recess, an inner surface of which defines the bearing surface 140 of the second body. As the projection of the first body 102 is urged into the recess of the second body 106, the conical surfaces wedge against one another to form a taper-lock connection. While conical surfaces are described in the example above, the male and female features can include concave or convex spherical surfaces, stepped surfaces, and so forth.

One or both of the bearing surfaces 130, 140 can include surface features for enhancing grip between the surfaces. For example, one or both surfaces can include teeth, grooves, roughening, surface textures or coatings, etc. In some embodiments, as shown in FIG. 1D, each bearing surface 130, 140 can include a plurality of teeth that extend radially outward from the rotation axis A1. The teeth can selectively interlock to maintain the bodies 102, 106 in one of a plurality of discrete rotational positions relative to one another.

The distal end 102d of the body 102 can define an interior cavity 132 in which a first end of the hinge pin 110 can be received. The cavity 132 can be open to the bearing surface 130 of the first body 102 and open to the first rod-receiving recess 104 as shown. In some embodiments, the cavity 132 can be a blind bore formed in the bearing surface 130 of the body 102 and intersecting with the first rod-receiving recess 104. At least one dimension of the cavity 132 can be greater than a corresponding dimension of the hinge pin 110 to allow the hinge pin to translate within the cavity along the rotation axis A1. As described further below, the cavity 132 can be dimensioned to limit the degree to which the body 102 can rotate relative to the hinge pin 110 about the axis A1.

The second body 106 can be identical or substantially identical to the first body 102, or can have any of the features or variations described above with respect to the first body 102. Accordingly, only a brief description of the second body 106 is provided here for the sake of brevity. The second body 106 can include proximal and distal ends 106p, 106d that define a proximal-distal axis A4. The proximal end 106p of the body 106 can include a pair of spaced apart arms 134, 136 that define the second rod-receiving recess 108 therebetween. A rod R2 disposed in the second rod-receiving recess 108 can have a central longitudinal rod axis A5. The second rod-receiving recess 108 can be open in a proximal direction, such that a rod R2 can be inserted into the recess by moving the rod distally with respect to the connector 100. Alternatively, the second rod-receiving recess 108 can be open in distal direction, open in a lateral direction, or closed such that the rod R2 must be translated along the axis A5 to insert the rod into the recess 108.

Each of the arms 134, 136 can include features 138 for retaining the saddle 122 within the body 106. The second body 106 can include an outer bearing surface 140 configured to contact and bear against the outer bearing surface 130 of the first body 102. The distal end 106d of the second body 106 can define an interior cavity 142 in which a second end of the hinge pin 110 can be received. The cavity 142 can be open to the bearing surface 140 of the second body 106 and open to the second rod recess 108 as shown. In some embodiments, the cavity 142 can be a blind bore formed in the bearing surface 140 of the body 106 and intersecting with the second rod recess 108. At least one dimension of the cavity 142 can be greater than a corresponding dimension of the hinge pin 110 to allow the hinge pin to translate within the cavity along the rotation axis A1. As described further below, the cavity 142 can be dimensioned to limit the degree to which the body 106 can rotate relative to the hinge pin 110 about the axis A1.

The bodies 102, 106 of the connector 100 can include various features for decreasing or increasing the center-to-center offset between the first and second rods R1, R2 when the rods are locked to the connector. In the illustrated embodiment, the bearing surfaces 130, 140 of the first and second bodies 102, 106 are obliquely angled with respect to the bodies' respective proximal-distal axes A2, A4. Accordingly, the rods R1, R2 move towards one another as they are advanced distally into the connector 100. This can advantageously reduce the center-to-center offset of the rods R1, R2, while preserving sufficient material thickness at the proximal ends of the bodies 102, 106 to withstand the relatively high forces subjected to the connector 100 during rod reduction, fastener tightening, and/or post-operative patient movement.

As another example, the bearing surfaces 130, 140 of the bodies 102, 106 can be parallel to the proximal-distal axes A2, A4, and instead the rod recesses 104, 108 can be obliquely angled or can follow a curved path with respect to the proximal-distal axes to bring the rods R1, R2 closer together.

As another example, the axis along which the first fastener 112 advances as it is tightened can be offset laterally from the first rod axis A3 when the first rod R1 is fully seated in the recess 104, or can be obliquely angled with respect to the proximal-distal axis A2 of the first body 102. Alternatively, or in addition, the axis along which the second fastener 114 advances as it is tightened can be offset laterally from the second rod axis A5 when the second rod R2 is fully seated in the recess 108, or can be obliquely angled with respect to the proximal-distal axis A4 of the second body 106.

The rotation axis A1 of the connector 100 can be perpendicular to the rod axis A3 and perpendicular to the rod axis A5. The rotation axis A1 can be perpendicular to the proximal-distal axis A2 of the first body, or can be obliquely angled with respect to the axis A2. The rotation axis A1 can be perpendicular to the proximal-distal axis A4 of the second body, or can be obliquely angled with respect to the axis A4. The proximal-distal axes A2, A4 of the bodies 102, 106 can be parallel to one another or can extend at an oblique angle with respect to one another.

Figure 1G:
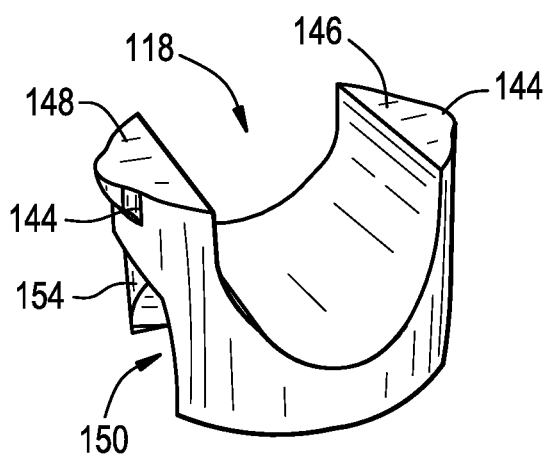
FIG. 1G is a perspective view of a first saddle of the connector of FIG. 1A.
Figure 1H:
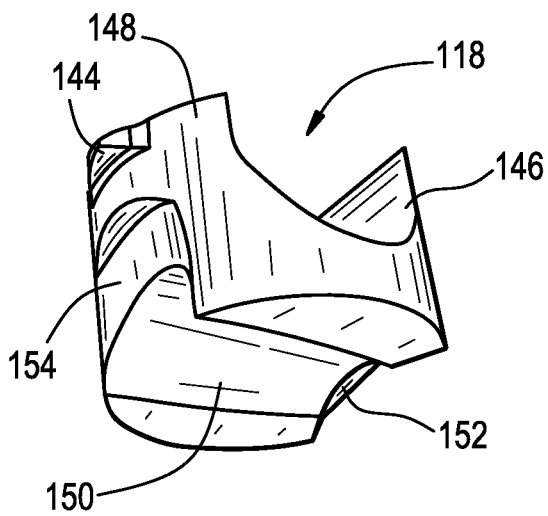
FIG. 1H is another perspective view of the first saddle of FIG. 1G.
Figure 1I:
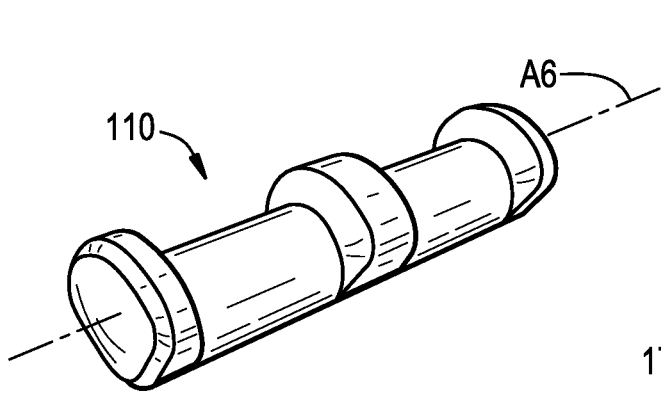
FIG. 1I is a perspective view of a hinge pin of the connector of FIG. 1A.

The first saddle 118 is shown in greater detail in FIGS. 1C, 1G, and 1H. The saddle 118 can be positioned within the body 102. The saddle 118 can be configured to translate within the body 102 along the axis A2, e.g., between proximal and distal limits defined by the interaction between the recesses 128 of the body 102 and projections 144 formed on the saddle.

The saddle 118 can be generally cylindrical with first and second arms 146, 148 extending in a proximal direction to respective free ends of the arms. The first and second arms 146, 148 can be aligned with the first and second arms 124, 126 of the body 102 such that a recess defined therebetween is aligned with the first rod-receiving recess 104. Accordingly, the first rod R1 can be simultaneously cradled between the arms 146, 148 of the saddle 118 and the arms 124, 126 of the body 102 when the rod is disposed in the first rod-receiving recess 104. The first and second arms 146, 148 of the saddle 118 can include projections 144 extending radially outward therefrom and configured to be received within the recesses 128 of the first body 102.

The distal-facing surface of the saddle 118 can define a recess 150 configured to receive at least a portion of the hinge pin 110. In the illustrated embodiment, the recess 150 is semi-cylindrical. The depth of the recess 150 can increase along the length of the recess as shown to account for a body geometry in which the proximal-distal axis A2 of the body is obliquely angled with respect to the rotation axis A1 of the hinge pin 110.

The saddle 118 can include one or more ramped, curved, or otherwise tapered surfaces configured to contact and bear against a counterpart surface of the hinge pin 110. For example, a depression formed in the outer surface of the first arm 146 of the saddle 118 can define a first bearing surface 152 that is a section of a cone. A depression formed in the outer surface of the second arm 148 of the saddle 118 can define a second bearing surface 154 that is a section of a cone.

The second saddle 122 can be identical or substantially identical to the first saddle 118, or can have any of the features or variations described above with respect to the first saddle 118. Accordingly, only a brief description of the second saddle 122 is provided here for the sake of brevity. The second saddle 122 can be positioned within the body 106. The saddle 122 can be configured to translate within the body 106 along the axis A4, e.g., between proximal and distal limits defined by the interaction between the recesses 138 of the body and projections 156 formed on the saddle.

The saddle 122 can be generally cylindrical with first and second arms 158, 160 extending in a proximal direction to respective free ends of the arms. The first and second arms 158, 160 can be aligned with the first and second arms 134, 136 of the body 106 such that a recess defined therebetween is aligned with the second rod-receiving recess 108. Accordingly, the second rod R2 can be simultaneously cradled between the arms 158, 160 of the saddle 122 and the arms 134, 136 of the body 106 when the rod is disposed in the second rod-receiving recess 108. The first and second arms 158, 160 of the saddle 122 can include projections 156 extending radially outward therefrom and configured to be received within the recesses 138 of the second body 106.

The distal-facing surface of the saddle 122 can define a recess 162 configured to receive at least a portion of the hinge pin 110. In the illustrated embodiment, the recess 162 is semi-cylindrical. The depth of the recess 162 can increase along the length of the recess as shown to account for a body geometry in which the proximal-distal axis A4 of the body 106 is obliquely angled with respect to the rotation axis A1 of the hinge pin 110.

The saddle 122 can include one or more ramped, curved, or otherwise tapered surfaces configured to contact and bear against a counterpart surface of the hinge pin 110. For example, a depression formed in the outer surface of the first arm 158 of the saddle 122 can define a first bearing surface 164 that is a section of a cone. A depression formed in the outer surface of the second arm 160 of the saddle 122 can define a bearing surface 166 that is a section of a cone.

The first fastener 112 can include an exterior thread configured to mate with the interior threads formed on the arms 124, 126 of the body 102 to allow the first fastener to be advanced or retracted along the axis A2 with respect to the body by rotating the first fastener about the axis A2. The first fastener 112 can include a driving interface 168 configured to receive a driver for applying a rotational force to the first fastener about the axis A2. The distal surface of the first fastener 112 can be configured to contact and bear against a rod R1 disposed in the first rod-receiving 104 recess to lock the rod to the connector 100. When tightened against the rod R1, the first fastener 112 can prevent the rod from translating relative to the connector 100 along the axis A3 and/or from rotating with respect to the connector about the axis A3. While a unitary set screw 112 is shown, it will be appreciated that other fasteners can be used instead or addition, such as a closure cap that advances and locks by quarter-turn rotation, a closure cap that slides in laterally without rotating, a nut that threads onto an exterior of the body, or a dual-component set screw with independently-rotatable inner and outer members, the inner member acting on the rod R1 and the outer member acting on the saddle 118.

The second fastener 114 can include an exterior thread configured to mate with the interior threads formed on the arms 134, 136 of the second body 106 to allow the second fastener to be advanced or retracted along the axis A4 with respect to the body by rotating the second fastener about the axis A4. The second fastener 114 can include a driving interface 170 configured to receive a driver for applying a rotational force to the second fastener 114 about the axis A4. The distal surface of the second fastener 114 can be configured to contact and bear against a rod R2 disposed in the second rod-receiving 108 recess to lock the rod to the connector 100. When tightened against the rod R2, the second fastener 114 can prevent the rod from translating relative to the connector 100 along the axis A5 and/or from rotating with respect to the connector about the axis A5. While a unitary set screw 114 is shown, it will be appreciated that other fasteners can be used instead or addition, such as a closure cap that advances and locks by quarter-turn rotation, a closure cap that slides in laterally without rotating, a nut that threads onto an exterior of the body, or a dual-component set screw with independently-rotatable inner and outer members, the inner member acting on the rod R2 and the outer member acting on the saddle 122.

The hinge pin 110 is shown in greater detail in FIGS. 1I-1L. As shown, the hinge pin 110 can include opposed first and second ends that define a central longitudinal axis A6 extending therebetween. The longitudinal axis A6 can be collinear with the rotation axis A1 of the connector 100. The hinge pin 110 can be formed as a substantially cylindrical shaft with one or more protrusions 172 extending radially outward therefrom. One or both side surfaces of the protrusions 172 can be ramped, curved, or otherwise tapered and configured to contact and bear against counterpart surfaces of the saddles 118, 122 or, in embodiments in which the saddles are omitted, against counterpart surfaces of the rods R1, R2. The illustrated hinge pin 110 includes at least first and second protrusion surfaces 116, 120 that each form sections of respective cones. The middle protrusion 172 of the hinge pin 110 can help keep the hinge pin centered in the cavities 132, 142 and maintain the bodies 102, 106 in a position in which the bearing surfaces 130, 140 are parallel.

Figure 1J:
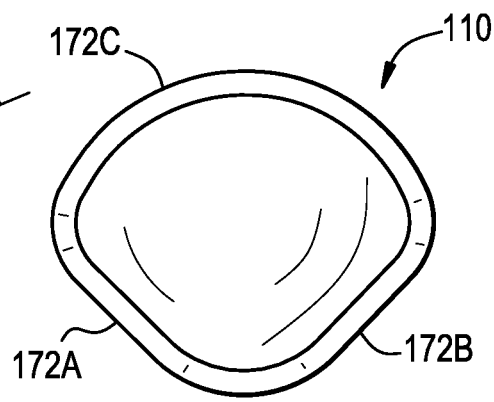
FIG. 1J is an end view of the hinge pin of FIG. 1I.
Figure 1K:
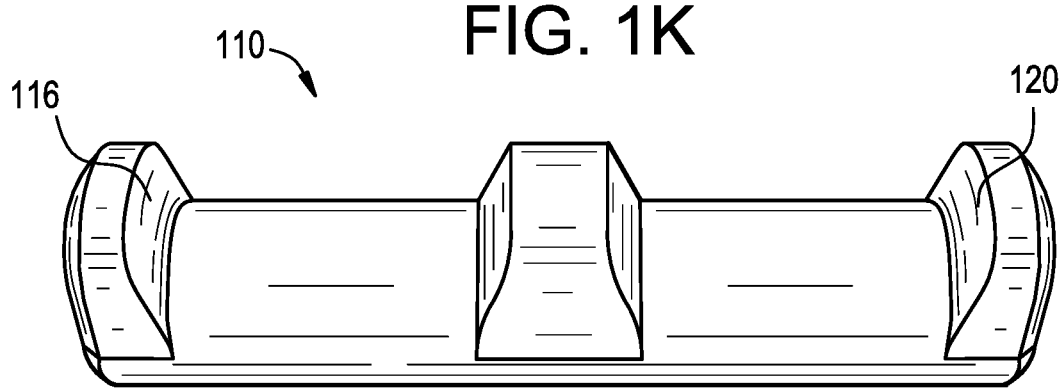
FIG. 1K is a side view of the hinge pin of FIG. 1I.
Figure 1L:
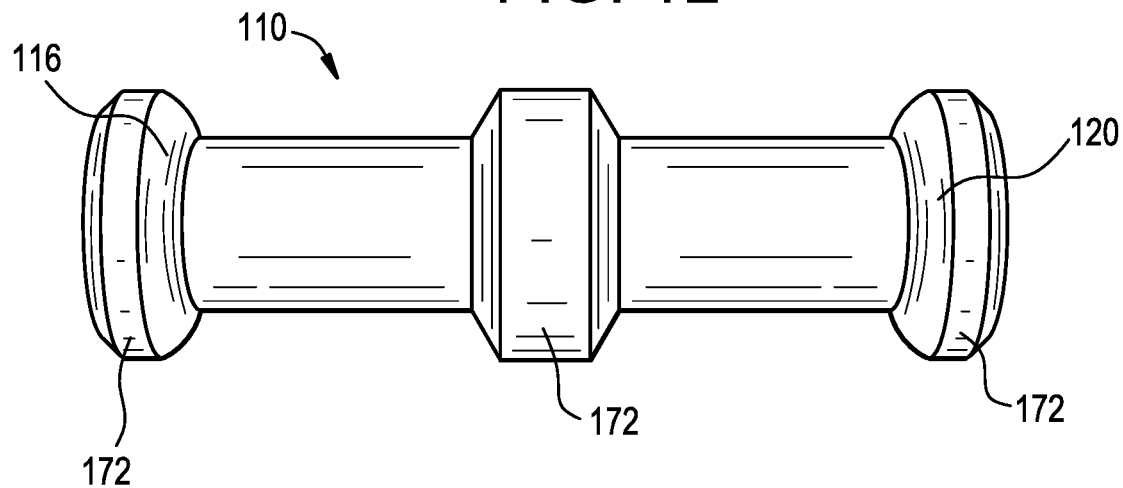
FIG. 1L is a top view of the hinge pin of FIG. 1I.

The protrusions 172 can extend around less than an entire circumference of the hinge pin 110, such that the protrusions have a non-cylindrical cross-section in a plane transverse to the axis A6. For example, as shown in FIG. 1J, each protrusion can define a lobe shape with first and second flat segments 172A, 172B joined by an arc 172C. The cavities 132, 142 formed in the bodies 102, 106 can have a corresponding shape, only with an arc that extends a greater degree about the circumference of the hinge pin 110. Accordingly, when the protrusions 172 are received within the cavities 132, 142, the degree to which the bodies 102, 106 are able to rotate relative to the hinge pin 110 about the axis A1 is limited to the difference between the arc length of the protrusions and the arc length of the cavity.

The connector 100 can be assembled by inserting one end of the hinge pin 110 into the cavity 132 of the first body 102 and the other end of the hinge pin into the cavity 142 of the second body 106. The saddles 118, 122 can be inserted into the proximal ends of the bodies 102, 106 and advanced distally until the projections 144, 156 of the saddles snap into the grooves 128, 138 of the bodies to retain the saddles therein. At this stage of assembly, even before locking rods within the connector 100, the saddles 118, 122 can interfere with the protrusions 172 of the hinge pin 110 to prevent the hinge pin from being removed from either of the first and second bodies 102, 106.

A first rod R1 can be seated in the first rod recess 104 and secured to the connector 100 by tightening the first fastener 112. As the first fastener 112 is tightened, the first rod R1 can be urged distally against the saddle 118, in turn urging the saddle distally against the hinge pin 110. As the saddle 118 is urged distally, the female conical surface 152 of the saddle bears against the male conical surface 116 of the hinge pin protrusion 172, applying a force to the hinge pin 110 that urges the hinge pin deeper into the cavity 132.

A second rod R2 can be seated in the second rod recess 108 and secured to the connector 100 by tightening the second fastener 114. As the second fastener 114 is tightened, the second rod R2 can be urged distally against the saddle 122, in turn urging the saddle distally against the hinge pin 110. As the saddle 122 is urged distally, the female conical surface 166 of the saddle bears against the male conical surface 120 of the hinge pin protrusion 172, applying a force to the hinge pin 110 that urges the hinge pin deeper into the cavity 142.

Before fully tightening one or both fasteners 112, 114, the bodies 102, 106 can be rotated relative to one another about the axis A1 as desired by the user. The fasteners 112, 114 can then be tightened to lock such relative rotation. In particular, the opposing forces applied to the hinge pin 110 by the saddles 118, 122 as the fasteners 112, 114 are tightened can cause the bodies 102, 106 to translate relative to one another along the axis A1, urging the bearing surfaces 130, 140 of the bodies into engagement with each other. Friction, mechanical interlock, or other forces between the bearing surfaces 130, 140 can be effective to lock relative rotation of the bodies 102, 106 about the axis A1.

FIGS. 2A-2E illustrate an exemplary embodiment of a connector 200. As shown, the connector 200 can include a first body 202 that defines a first rod-receiving recess or channel 204 and a second body 206 that defines a second rod-receiving recess or channel 208. The first and second bodies 202, 206 can be connected to one another at least in part by a hinge pin 210. The hinge pin 210 can define a rotation axis A1 about which the first and second bodies 202, 206 can rotate relative to one another. The connector 200 can include first and second fasteners 212, 214 configured to secure respective first and second rods R1, R2 or other fixation elements to the connector 200.

At least one of the fasteners 212, 214 can further be configured to urge the first and second bodies 202, 206 towards one another and thereby lock relative rotation of the first and second bodies about the rotation axis A1. For example, the first fastener 212 can be tightened to secure a first rod R1 within the first body 202 and to apply a force to a first ramped, curved, or otherwise tapered surface 216 of the hinge pin 210 to draw the first and second bodies 202, 206 towards one another, locking rotation therebetween. In the illustrated embodiment, a force applied by the first fastener 212 is transferred to the hinge pin 210 through the first rod R1. In other arrangements, a saddle of the type described above can be disposed between the first rod R1 and the hinge pin 210. In still further arrangements, the first fastener 212 can bear directly against a saddle. For example, the first fastener 212 can include an outer set screw that bears against a saddle to lock relative rotation of the bodies 202, 206, and an inner set screw that bears against the first rod R1 to secure the first rod to the connector 200.

The second fastener 214 can be tightened to secure a second rod R2 within the second body 206. The second fastener 214 can bear directly against the second rod R2, or against an intermediate rod pusher 222 as shown.

The ability to rotate the first and second bodies 202, 206 relative to one another about the rotation axis A1 can advantageously allow first and second rods R1, R2 to be locked together even when the rods are obliquely angled with respect to one another, e.g., in the sagittal plane or in the coronal plane. The connector 200 can be particularly useful in connecting tandem rods of a spinal fixation construct across the cervical-thoracic (CT) junction of a patient. For example, the connector 200 can secure the rods R1, R2 in a laterally-offset arrangement to accommodate the different screw trajectories that may occur at the CT junction. By way of further example, the ability of the connector 200 to articulate can allow a cervical rod and a thoracic rod to be locked to one another at an oblique angle in the sagittal plane, e.g., to restore natural lordosis or kyphosis. The connector 200 can also be particularly useful in spinal deformity correction and other procedures in which multiple angled rods are to be coupled to one another.

The first body 202 can include proximal and distal ends 202p, 202d that define a proximal-distal axis A2. The proximal end 202p of the body 202 can include a pair of spaced apart arms 224, 226 that define the first rod-receiving recess 204 therebetween. A rod R1 disposed in the first rod-receiving recess 204 can have a central longitudinal rod axis A3. The first rod-receiving recess 204 can be open in a proximal direction, such that a rod R1 can be inserted into the recess by moving the rod distally with respect to the connector 200. Alternatively, the first rod-receiving recess 204 can be open in distal direction, open in a lateral direction, or closed such that the rod R1 must be translated along the axis A3 to insert the rod into the recess 204.

Each of the arms 224, 226 can extend from the distal portion 202d of the body 202 to a free end. The outer surfaces of each of the arms 224, 226 can include a feature (not shown), such as a recess, dimple, notch, projection, or the like, to facilitate coupling of the connector 200 to various instruments. For example, the outer surface of each arm 224, 226 can include an arcuate groove at the respective free end of the arms for attaching the connector 200 to an extension tower or retractor. The arms 224, 226 can include or can be coupled to extension or reduction tabs (not shown) that extend proximally from the body 202 to functionally extend the length of the arms 224, 226. The extension tabs can facilitate insertion and reduction of a rod or other implant, as well as insertion and locking of the first fastener 212. The extension tabs can be configured to break away or otherwise be separated from the arms 224, 226.

The inner surfaces of each of the arms 224, 226 can be configured to mate with the first fastener 212. For example, the inner surfaces of the arms 224, 226 can include threads that correspond to external threads formed on the first fastener 212. Accordingly, rotation of the first fastener 212 with respect to the body 202 about the axis A2 can be effective to translate the first fastener with respect to the body axially along the axis A2.

The first body 202 can include an outer bearing surface 230 configured to contact and bear against a corresponding bearing surface 240 of the second body 206. The respective bearing surfaces 230, 240 of the bodies 202, 206 can bear against one another to lock relative rotation between the bodies as they are urged towards one another. In the illustrated embodiment, the bearing surfaces 230, 240 of the first and second bodies 202, 206 are defined by complementary male and female structures of the first and second bodies 202, 206. As shown, the first body 202 can include a conical male projection, an outer surface of which defines the bearing surface 230 of the first body, and the second body 206 can include a conical female recess, an inner surface of which defines the bearing surface 240 of the second body. As the projection of the first body 202 is urged into the recess of the second body 206, the conical surfaces 230, 240 wedge against one another to form a taper-lock connection. While conical surfaces are described in the example above, the male and female features can include concave or convex spherical surfaces, stepped surfaces, and so forth. It will be appreciated that various other arrangements can be used instead or in addition, such as opposed planar surfaces configured to frictionally-engage one another as in the connector 100 described above.

One or both of the bearing surfaces 230, 240 can include surface features for enhancing grip between the surfaces. For example, one or both surfaces can include teeth, grooves, roughening, surface textures or coatings, etc. In some embodiments, each bearing surface 230, 240 can include a plurality of teeth that extend radially outward from the rotation axis A1. The teeth can selectively interlock to maintain the bodies 202, 206 in one of a plurality of discrete rotational positions relative to one another.

The distal end 202d of the body 202 can define an interior cavity 232 in which a first end of the hinge pin 210 can be received. The cavity 232 can be open to the bearing surface 230 of the first body 202 and open to the first rod-receiving recess 204 as shown. In some embodiments, the cavity 232 can be a blind bore formed in the bearing surface 230 of the body 202 and intersecting with the first rod-receiving recess 204. At least one dimension of the cavity 232 can be greater than a corresponding dimension of the hinge pin 210 to allow the hinge pin to translate within the cavity along the rotation axis A1.

Figure 2A:
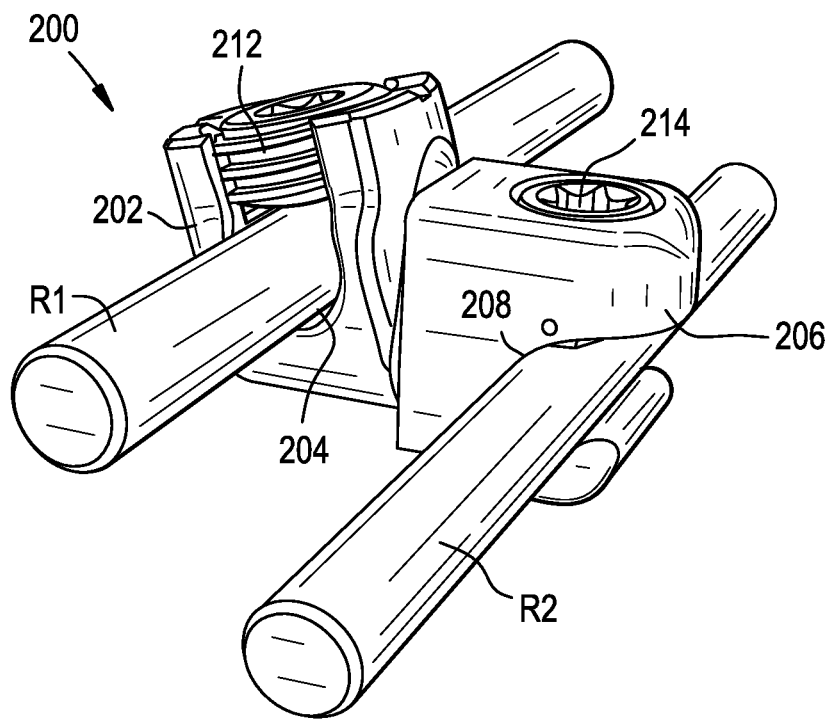
FIG. 2A is a perspective view of a connector, shown with first and second rods.
Figure 2B:
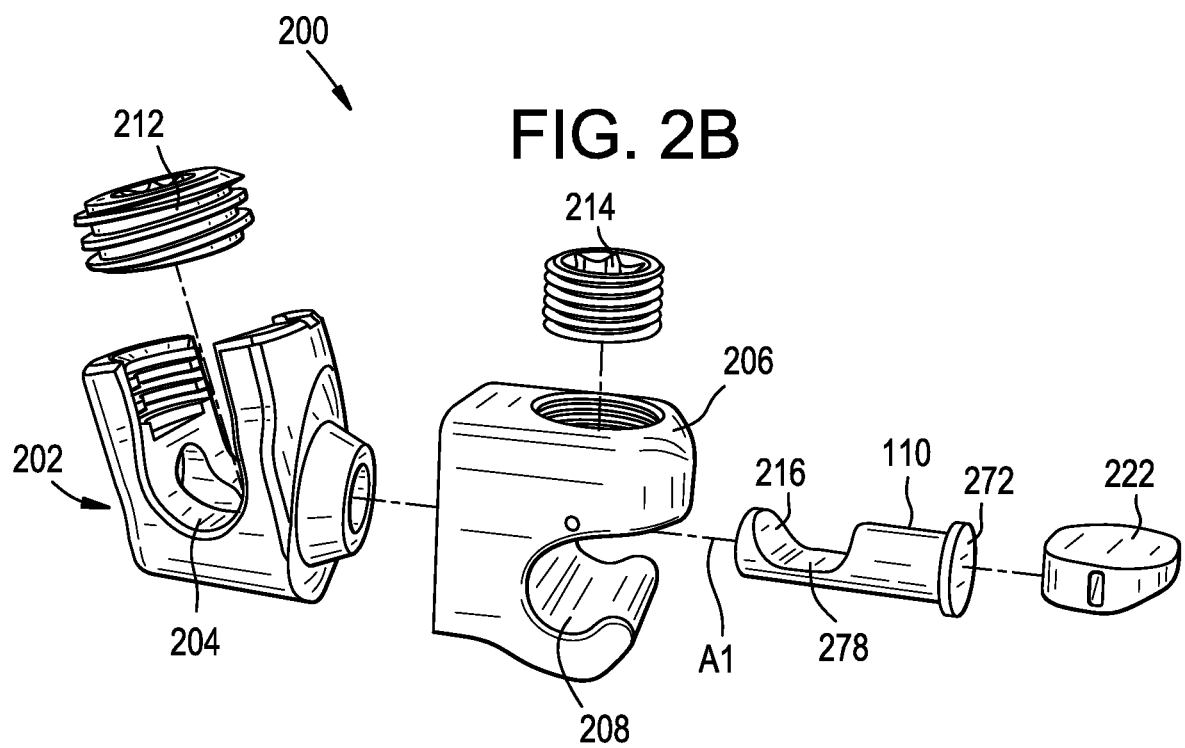
FIG. 2B is an exploded perspective view of the connector of FIG. 2A.
Figure 2C:
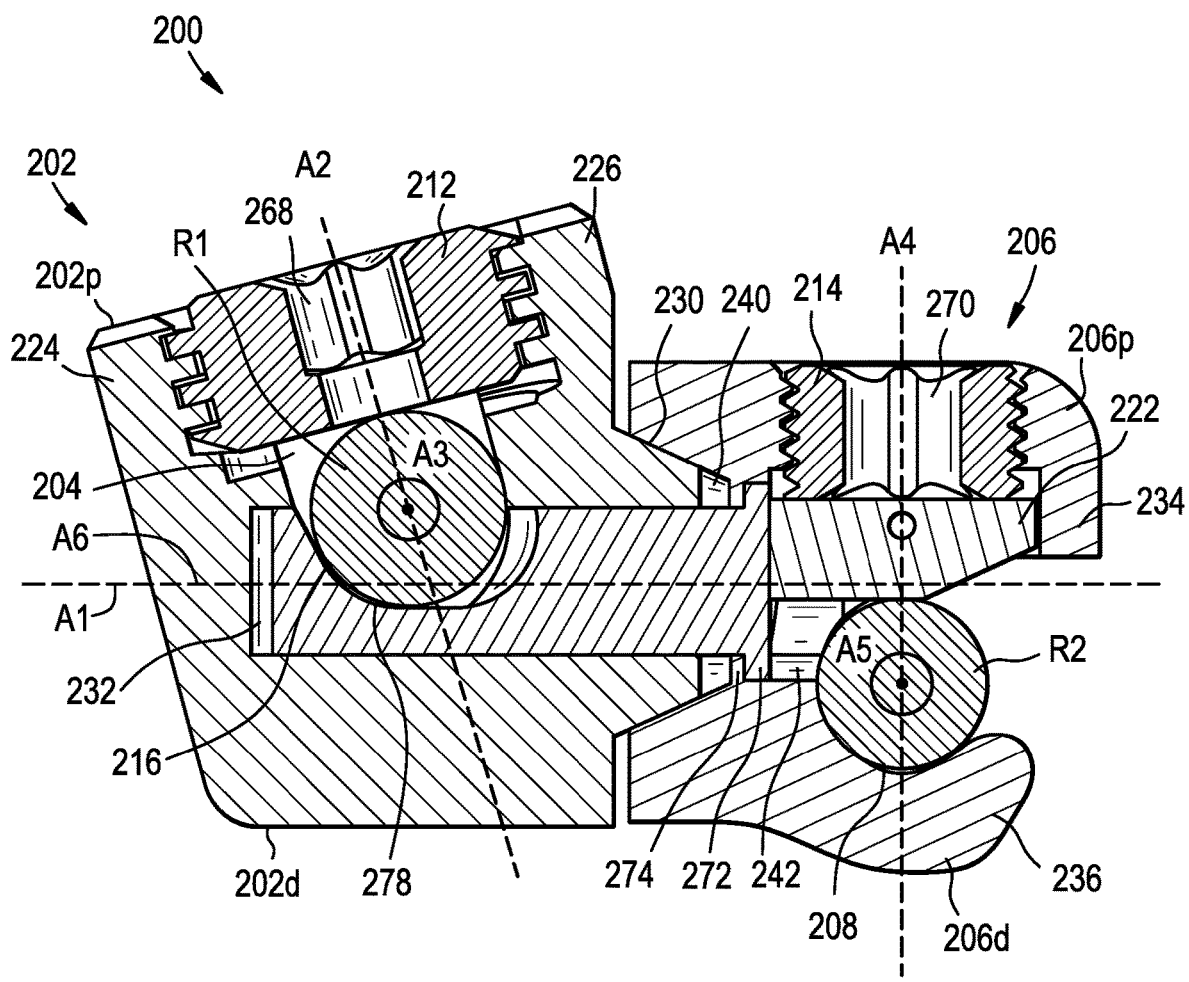
FIG. 2C is a sectional side view of the connector and rods of FIG. 2A.
Figure 2D:
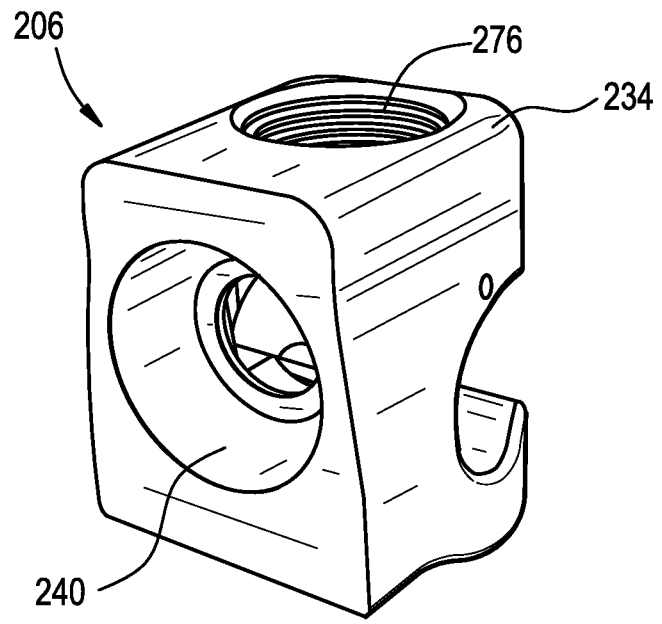
FIG. 2D is a perspective view of a second body of the connector of FIG. 2A.
Figure 2E:
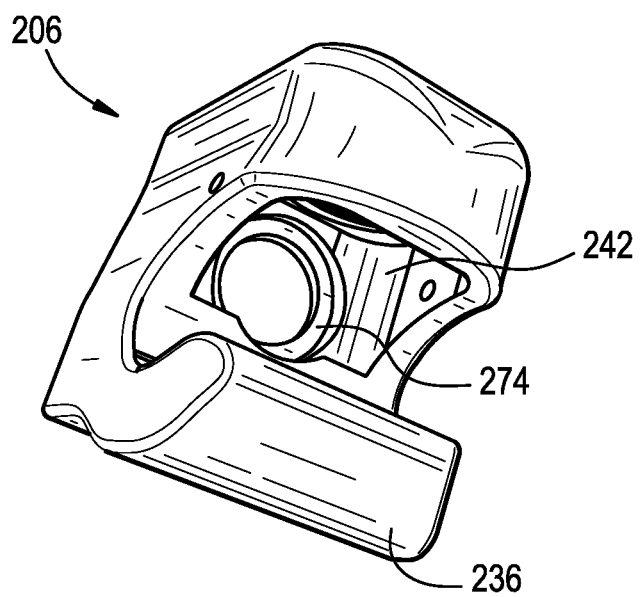
FIG. 2E is another perspective view of the second body of FIG. 2A.

The second body 202 is shown in greater detail in FIGS. 2C, 2D, and 2E. The second body 206 can include proximal and distal ends 206p, 206d that define a proximal-distal axis A4. The body 206 can include a pair of spaced apart arms 234, 236 that define the second rod-receiving recess 208 therebetween. A rod R2 disposed in the second rod-receiving recess 208 can have a central longitudinal rod axis A5. The second rod-receiving recess 208 can be open in a lateral direction, as shown, such that a rod R2 can be inserted into the recess by moving the rod laterally with respect to the connector 200. Alternatively, the second rod-receiving recess 208 can be open in a proximal direction, open in a distal direction, or closed such that the rod R2 must be translated along the axis A5 to insert the rod into the recess 208.

The second body 206 can include an outer bearing surface 240 configured to contact and bear against the outer bearing surface 230 of the first body 202. The second body 206 can define an interior cavity 242 in which a second end of the hinge pin 210 can be received. The cavity 242 can be open to the bearing surface 240 of the second body 206 and open to the second rod recess 208 as shown. The cavity 242 can include a shoulder 274 configured to limit translation of the hinge pin 210 relative to the body 206 along the axis A1.

A rod pusher 222 can be disposed within the cavity 242 and can be configured to bear against the second rod R2. The rod pusher 222 can be coupled to the second body 206 by a bias element configured to bias the rod pusher towards the rod R2, e.g., to provide a "snap and drag" effect when seating the rod in the second recess 208. Further details on such features can be found in U.S. application Ser. No. 15/158,127 filed on May 18, 2016 and entitled "IMPLANT CONNECTORS AND RELATED METHODS," now issued as U.S. Pat. No. 10,517,647, which is hereby incorporated by reference in its entirety.

At least one of the arms 234, 236 of the second body 206 can include an opening 276 configured to receive the second fastener 214 therein. For example, as shown, the first arm 234 can include a threaded opening 276 in which the second fastener 214 can be advanced to urge the rod pusher 222 against a second rod R2 seated in the second rod-receiving recess 208.

The bodies 202, 206 of the connector 200 can include various features for decreasing or increasing the center-to-center offset between the first and second rods R1, R2 when the rods are locked to the connector. In the illustrated embodiment, the outer surface of the first body 202 that opposes the second body 206 is obliquely angled with respect to the proximal-distal axis A2. Accordingly, the rods R1, R2 move towards one another as they are advanced into the connector 200. This can advantageously reduce the center-to-center offset of the rods R1, R2, while preserving sufficient material thickness at the proximal end of the first body 202 to withstand the relatively high forces subjected to the connector 200 during rod reduction, fastener tightening, and/or post-operative patient movement.

As another example, the opposing outer surfaces of the bodies 202, 206 can be parallel to the proximal-distal axes A2, A4, and instead the rod recesses 204, 208 can be obliquely angled or can follow a curved path with respect to the proximal-distal axes to bring the rods R1, R2 closer together.

As another example, the axis along which the first fastener 212 advances as it is tightened can be offset laterally from the first rod axis A3 when the first rod R1 is fully seated in the recess 204, or can be obliquely angled with respect to the proximal-distal axis A2 of the first body 202. Alternatively, or in addition, the axis along which the second fastener 214 advances as it is tightened can be offset laterally from the second rod axis A5 when the second rod R2 is fully seated in the recess 208, or can be obliquely angled with respect to the proximal-distal axis A4 of the second body 206.

The rotation axis A1 of the connector 200 can be perpendicular to the rod axis A3 and perpendicular to the rod axis A5. The rotation axis A1 can be perpendicular to the proximal-distal axis A2 of the first body, or can be obliquely angled with respect to the axis A2. The rotation axis A1 can be perpendicular to the proximal-distal axis A4 of the second body, or can be obliquely angled with respect to the axis A4. The proximal-distal axes A2, A4 of the bodies 202, 206 can be parallel to one another or can extend at an oblique angle with respect to one another.

The first fastener 212 can include an exterior thread configured to mate with the interior threads formed on the arms 224, 226 of the body 202 to allow the first fastener to be advanced or retracted along the axis A2 with respect to the body by rotating the first fastener about the axis A2. The first fastener 212 can include a driving interface 268 configured to receive a driver for applying a rotational force to the first fastener about the axis A2. The distal surface of the first fastener 212 can be configured to contact and bear against a rod R1 disposed in the first rod-receiving 204 recess to lock the rod to the connector 200. When tightened against the rod R1, the first fastener 212 can prevent the rod from translating relative to the connector 200 along the axis A3 and/or from rotating with respect to the connector about the axis A3. While a unitary set screw 212 is shown, it will be appreciated that other fasteners can be used instead or addition, such as a closure cap that advances and locks by quarter-turn rotation, a closure cap that slides in laterally without rotating, a nut that threads onto an exterior of the body, or a dual-component set screw with independently-rotatable inner and outer members, the inner member acting on the rod R1 and the outer member acting on a saddle of the type described above.

The second fastener 214 can include an exterior thread configured to mate with the interior threads formed in the first arm 234 of the second body 206 to allow the second fastener to be advanced or retracted along the axis A4 with respect to the body by rotating the second fastener about the axis A4. The second fastener 214 can include a driving interface 270 configured to receive a driver for applying a rotational force to the second fastener 214 about the axis A4. The distal surface of the second fastener 214 can be configured to contact and bear against the rod pusher 222 or, in embodiments in which the rod pusher is omitted, against a rod R2 disposed in the second rod-receiving 208 recess to lock the rod to the connector 200. When tightened, the second fastener 214 can prevent the rod R2 from translating relative to the connector 200 along the axis A5 and/or from rotating with respect to the connector about the axis A5. While a unitary set screw 214 is shown, it will be appreciated that other fasteners can be used instead or addition, such as a closure cap that advances and locks by quarter-turn rotation, a closure cap that slides in laterally without rotating, or a nut that threads onto an exterior of the body.

The hinge pin 210 can include opposed first and second ends that define a central longitudinal axis A6 extending therebetween. The longitudinal axis A6 can be collinear with the rotation axis A1 of the connector 200. The hinge pin 210 can be formed as a substantially cylindrical shaft. The portion of the hinge pin 210 received within the first body 202 can include a rod seat 278. The portion of the hinge pin 210 received within the second body 206 can include a protrusion 272 extending radially outward therefrom.

The protrusion 272 can be seated in and can bear against the shoulder 274 formed in the second body 206. Accordingly, lateral translation of the hinge pin 210 along the axis A1, e.g., as the first rod R1 is urged against the hinge pin, can cause the second body 206 to be urged towards the first body to lock relative rotation therebetween. The rod seat 278 can be ramped, curved, or otherwise tapered and configured to contact and bear against the first rod R1. The rod seat 278 can have a width parallel to the axis A1 that is greater than the diameter of the first rod R1 and/or greater than the width of the first rod-receiving recess 204. The rod seat 278 can be located along the length of the hinge pin 210 at a position in which a lateral sidewall 216 of the rod seat interferes with a rod R1 as the rod is seated in the first rod-receiving recess 204. As the rod R1 is advanced into the first rod-receiving recess 204, it can bear against the lateral sidewall 216 of the rod seat 278 to cause the hinge pin 210 to translate laterally along the axis A1, pulling the second body 206 towards the first body 202 to lock relative rotation therebetween. The hinge pin 210 can be rotatable relative to the first and second bodies 202, 206 about the axis A1, such that the floor of the rod seat 278 remains aligned with a floor of the first rod-receiving recess 204 or is moved into such alignment automatically as a rod R1 is seated therein. Prior to seating the first rod R1, the hinge pin 210 can be retained within the cavity 232 of the first body 202 using various techniques, such as swaging or a retention pin that limits axial translation of the hinge pin 210 relative to the body without limiting rotation of the hinge pin relative to the body about the axis A1.

The connector 200 can be assembled by inserting the hinge pin 210 through the cavity 242 of the second body 206 to seat the protrusion 272 of the hinge pin against the shoulder 274 and then installing the rod pusher 222 within the second body to retain the hinge pin therein. The free end of the hinge pin 210 can then be inserted into the cavity 232 of the first body 202 and retained therein with a retention feature of the type described above. At this stage of assembly, even before locking rods within the connector 200, the hinge pin 210 can be prevented from being removed from either of the first and second bodies 202, 206.

A second rod R2 can be seated in the second rod recess 208 and secured to the connector 200 by tightening the second fastener 214. As the second fastener 214 is tightened, the rod pusher 222 can be urged distally against the second rod R2 to lock the rod to the connector 200. The second body 206 can remain free to rotate relative to the first body 202 about the axis A1 even after the second rod R2 is locked to the connector 200.

A first rod R1 can be seated in the first rod recess 204 and secured to the connector 200 by tightening the first fastener 212. As the first fastener 212 is tightened, the first rod R1 can be urged distally against the rod seat 278 of the hinge pin 210, applying a force to the hinge pin that urges the hinge pin deeper into the cavity 232.

Before fully tightening one or both fasteners 212, 214, the bodies 202, 206 can be rotated relative to one another about the axis A1 as desired by the user. The fastener 212 can then be tightened to lock such relative rotation. In particular, the force applied to the hinge pin 210 by the first rod R1 when the fastener 212 is tightened can cause the bodies 202, 206 to translate relative to one another along the axis A1, urging the bearing surfaces 230, 240 of the bodies into engagement with each other. Friction, mechanical interlock, or other forces between the bearing surfaces 230, 240 can be effective to lock relative rotation of the bodies 202, 206 about the axis A1. It will be appreciated that the connector 200 can allow locking of the second rod R2 to the connector and locking of the rotational degree-of-freedom of the connector to be performed independently of one another.

FIGS. 3A-3L illustrate an exemplary embodiment of a connector 300. As shown, the connector 300 can include a first body 302 that defines a first rod-receiving recess or channel 304 and a second body 306 that defines a second rod-receiving recess or channel 308. The first and second bodies 302, 306 can be connected to one another at least in part by a hinge pin 310. The hinge pin 310 can define a rotation axis A1 about which the first and second bodies 302, 306 can rotate relative to one another. The connector 300 can include first and second fasteners 312, 314 configured to secure respective first and second rods R1, R2 or other fixation elements to the connector 300.

At least one of the fasteners 312, 314 can further be configured to urge the first and second bodies 302, 306 towards one another and thereby lock relative rotation of the first and second bodies about the rotation axis A1. For example, the second fastener 314 can be tightened to secure a second rod R2 within the second body 306 and to apply a force to a ramped, curved, or otherwise tapered surface 320 of the hinge pin 310 to draw the first and second bodies 302, 306 towards one another, locking rotation therebetween. In the illustrated embodiment, a force applied by the second fastener 314 is transferred to the hinge pin 310 through the second rod R2 and through a saddle 322 disposed between the second rod and the hinge pin. In other arrangements, the saddle 322 can be omitted and the second rod R2 can bear directly against the hinge pin 310. In still further arrangements, the second fastener 314 can bear directly against the saddle 322. For example, the second fastener 314 can include an outer set screw that bears against the saddle 322 to lock relative rotation of the bodies 302, 306, and an inner set screw that bears against the second rod R2 to secure the second rod to the connector 300.

The first fastener 312 can be tightened to secure a first rod R1 within the first body 302. The first fastener 312 can bear directly against the first rod R1 as shown, or against an intermediate rod pusher of the type described above with respect to the connector 200.

The ability to rotate the first and second bodies 302, 306 relative to one another about the rotation axis A1 can advantageously allow first and second rods R1, R2 to be locked together even when the rods are obliquely angled with respect to one another, e.g., in the sagittal plane or in the coronal plane. The connector 300 can be particularly useful in connecting tandem rods of a spinal fixation construct across the cervical-thoracic (CT) junction of a patient. For example, the connector 300 can secure the rods R1, R2 in a laterally-offset arrangement to accommodate the different screw trajectories that may occur at the CT junction. By way of further example, the ability of the connector 300 to articulate can allow a cervical rod and a thoracic rod to be locked to one another at an oblique angle in the sagittal plane, e.g., to restore natural lordosis or kyphosis. The connector 300 can also be particularly useful in spinal deformity correction and other procedures in which multiple angled rods are to be coupled to one another.

Figure 3A:
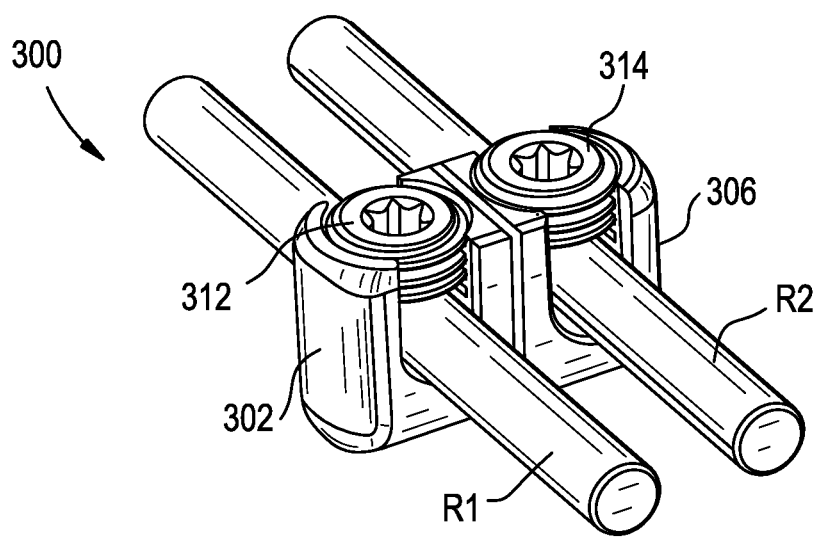
FIG. 3A is a perspective view of a connector, shown with first and second rods.
Figure 3B:
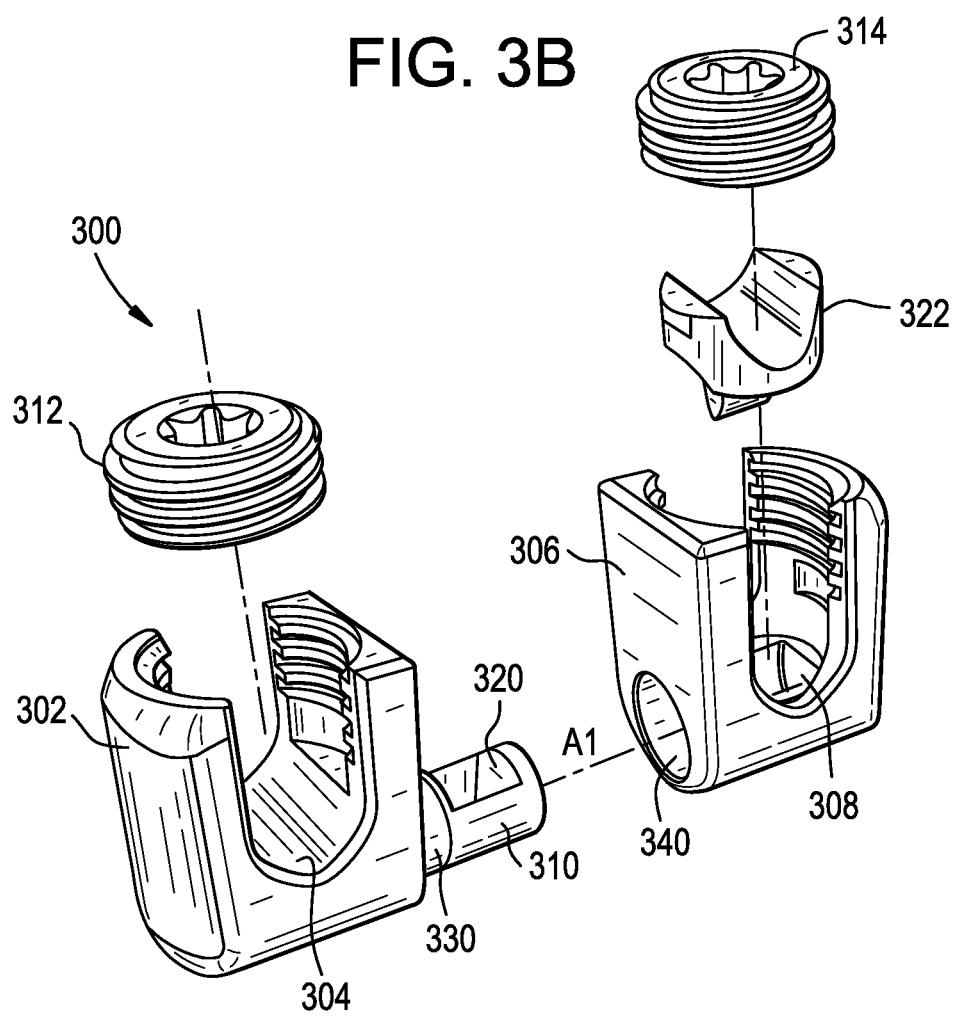
FIG. 3B is an exploded perspective view of the connector of FIG. 3A.
Figure 3C:
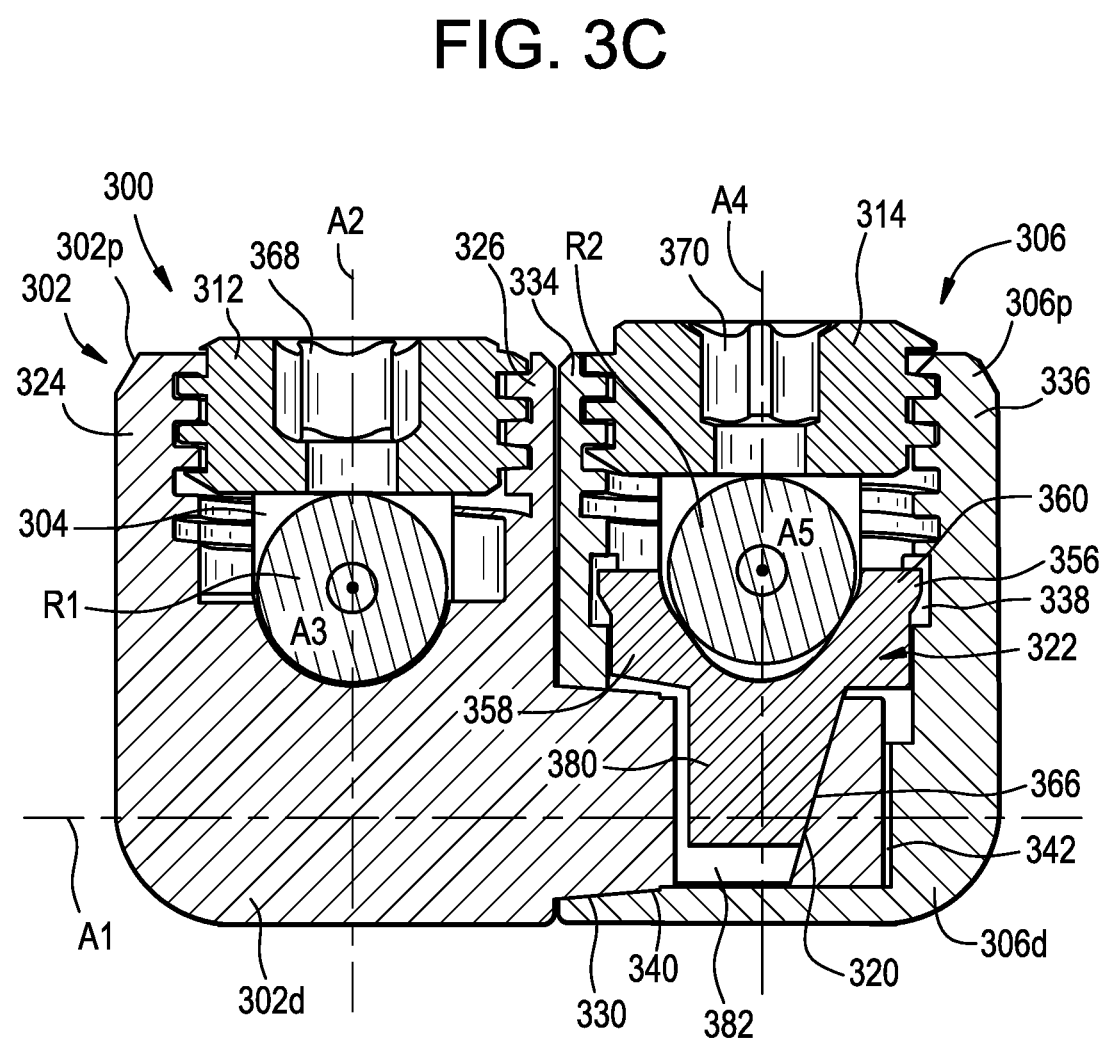
Figure 3D:
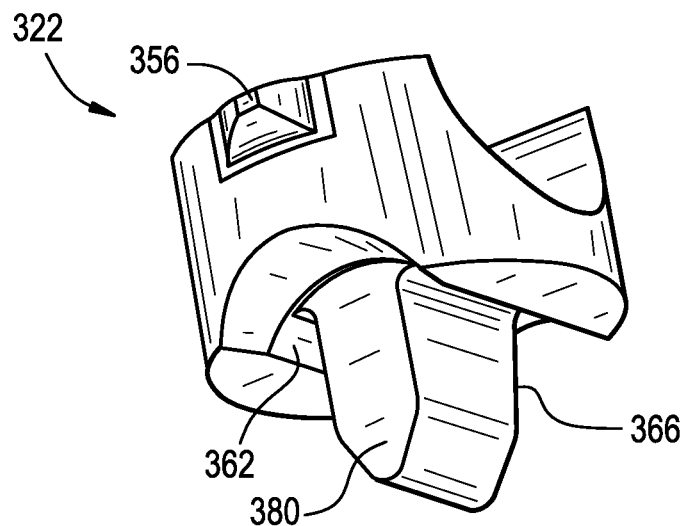
FIG. 3D is a perspective view of a saddle of the connector of FIG. 3A.
Figure 3E:
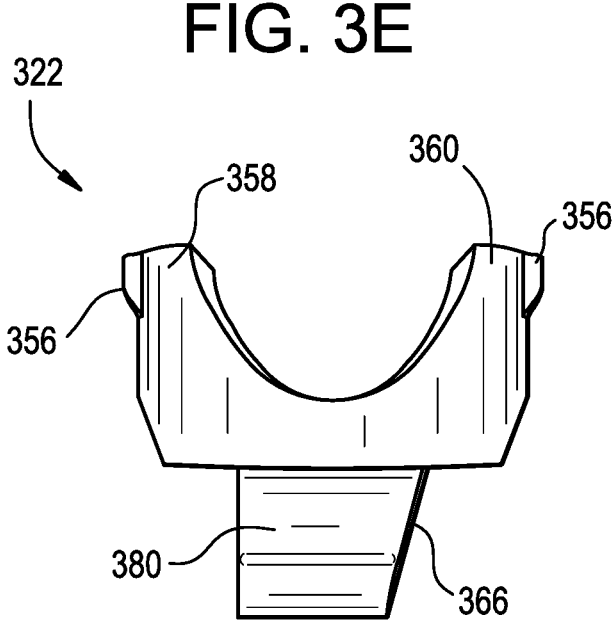
FIG. 3E is a side view of the saddle of FIG. 3D.
Figure 3F:
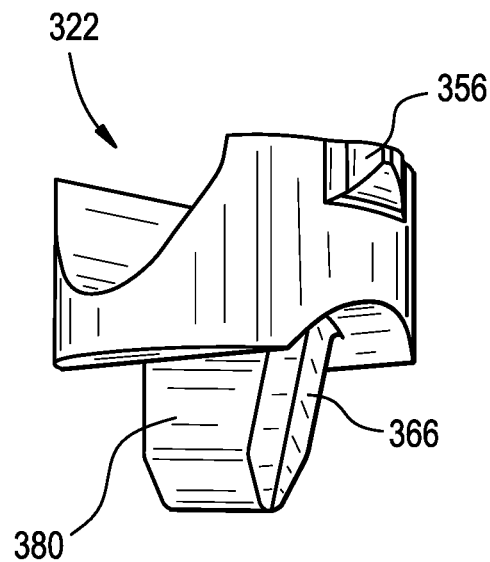
FIG. 3F is another perspective view of the saddle of FIG. 3D.
Figure 3G:
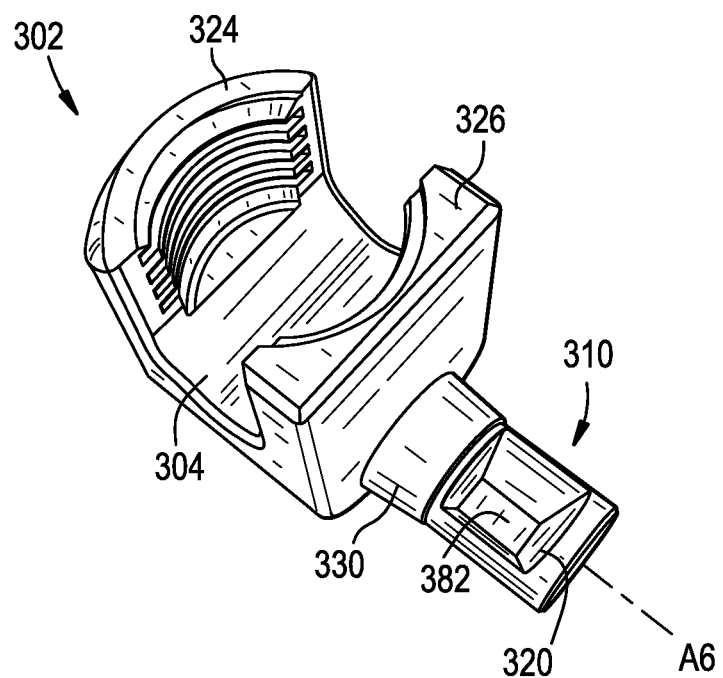
FIG. 3G is a perspective view of a first body of the connector of FIG. 3A.

The first body 302 is shown in greater detail in FIGS. 3C and 3G. The first body 302 can include proximal and distal ends 302p, 302d that define a proximal-distal axis A2. The proximal end 302p of the body 302 can include a pair of spaced apart arms 324, 326 that define the first rod-receiving recess 304 therebetween. A rod R1 disposed in the first rod-receiving recess 304 can have a central longitudinal rod axis A3. The first rod-receiving recess 304 can be open in a proximal direction, such that a rod R1 can be inserted into the recess by moving the rod distally with respect to the connector 300. Alternatively, the first rod-receiving recess 304 can be open in distal direction, open in a lateral direction, or closed such that the rod R1 must be translated along the axis A3 to insert the rod into the recess 304.

Each of the arms 324, 326 can extend from the distal portion 302d of the body 302 to a free end. The outer surfaces of each of the arms 324, 326 can include a feature (not shown), such as a recess, dimple, notch, projection, or the like, to facilitate coupling of the connector 300 to various instruments. For example, the outer surface of each arm 324, 326 can include an arcuate groove at the respective free end of the arms for attaching the connector 300 to an extension tower or retractor. The arms 324, 326 can include or can be coupled to extension or reduction tabs (not shown) that extend proximally from the body 302 to functionally extend the length of the arms 324, 326. The extension tabs can facilitate insertion and reduction of a rod or other implant, as well as insertion and locking of the first fastener 312. The extension tabs can be configured to break away or otherwise be separated from the arms 324, 326.

The inner surfaces of each of the arms 324, 326 can be configured to mate with the first fastener 312. For example, the inner surfaces of the arms 324, 326 can include threads that correspond to external threads formed on the first fastener 312. Accordingly, rotation of the first fastener 312 with respect to the body 302 about the axis A2 can be effective to translate the first fastener with respect to the body axially along the axis A2.

The first body 302 can include an outer bearing surface 330 configured to contact and bear against a corresponding bearing surface 340 of the second body 306. The respective bearing surfaces 330, 340 of the bodies 302, 306 can bear against one another to lock relative rotation between the bodies as they are urged towards one another. In the illustrated embodiment, the bearing surfaces 330, 340 of the first and second bodies 302, 306 are defined by complementary male and female structures of the first and second bodies 302, 306. As shown, the first body 302 can include a conical male projection, an outer surface of which defines the bearing surface 330 of the first body, and the second body 306 can include a conical female recess, an inner surface of which defines the bearing surface 340 of the second body. As the projection of the first body 302 is urged into the recess of the second body 306, the conical surfaces 330, 340 wedge against one another to form a taper-lock connection. While conical surfaces are described in the example above, the male and female features can include concave or convex spherical surfaces, stepped surfaces, and so forth. It will be appreciated that various other arrangements can be used instead or in addition, such as opposed planar surfaces configured to frictionally-engage one another as in the connector 100 described above.

One or both of the bearing surfaces 330, 340 can include surface features for enhancing grip between the surfaces. For example, one or both surfaces can include teeth, grooves, roughening, surface textures or coatings, etc. In some embodiments, each bearing surface 330, 340 can include a plurality of teeth that extend radially outward from the rotation axis A1. The teeth can selectively interlock to maintain the bodies 302, 306 in one of a plurality of discrete rotational positions relative to one another.

As described further below, the hinge pin 310 can be formed integrally with the first body 302. The hinge pin 310 can project laterally from the distal end 302d of the first body 302 along the axis A1. The bearing surface 330 of the first body 302 can be an exterior surface of the integrally-formed hinge pin 310.

Figure 3H:
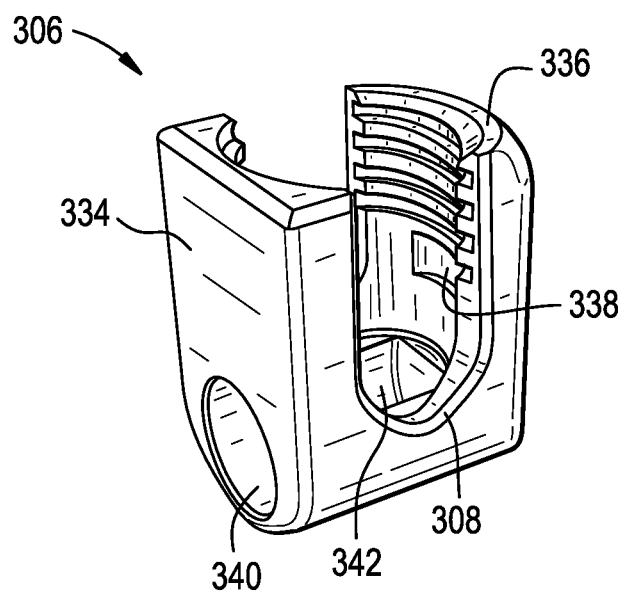
FIG. 3H is a perspective view of a second body of the connector of FIG. 3A.
Figure 3I:
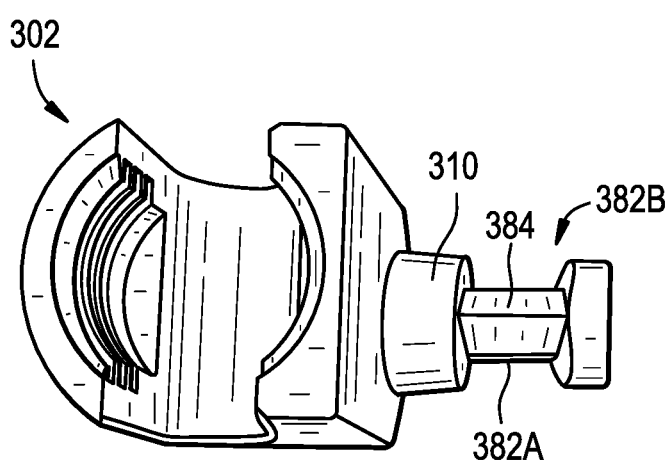
FIG. 3I is a top view of an alternate first body of the connector of FIG. 3A.
Figure 3J:
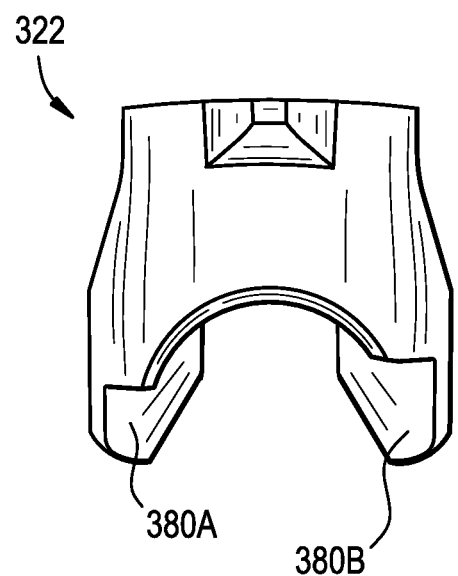
FIG. 3J is an end view of an alternate saddle of the connector of FIG. 3A
Figure 3K:
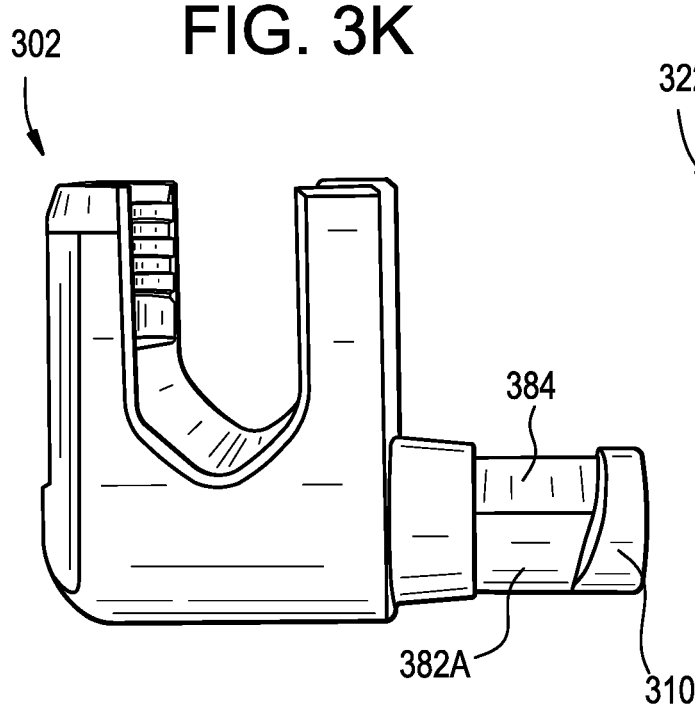
FIG. 3K is a side view of the alternate first body of FIG. 3I.
Figure 3L:
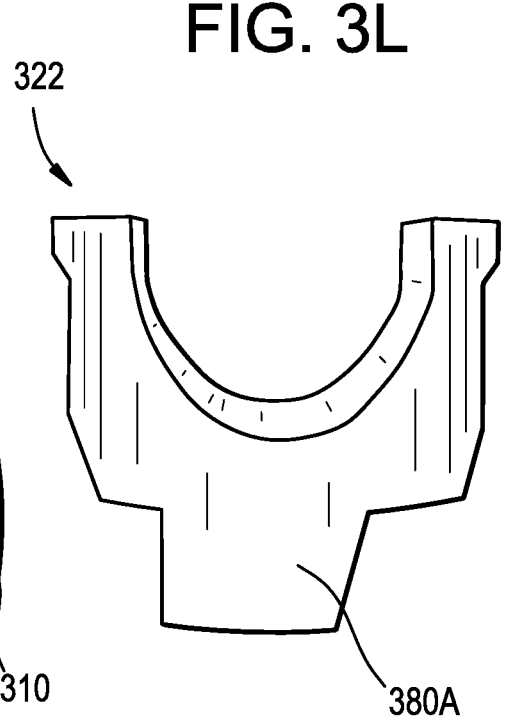
FIG. 3L is a side view of the alternate saddle of FIG. 3J.

The second body 302 is shown in greater detail in FIGS. 3C and 3H. Except as described below, the second body 306 can be identical or substantially identical to the first body 302, or can have any of the features or variations described above with respect to the first body 302. Accordingly, only a brief description of the second body 306 is provided here for the sake of brevity. The second body 306 can include proximal and distal ends 306p, 306d that define a proximal-distal axis A4. The proximal end 306p of the body 306 can include a pair of spaced apart arms 334, 336 that define the second rod-receiving recess 308 therebetween. A rod R2 disposed in the second rod-receiving recess 308 can have a central longitudinal rod axis A5. The second rod-receiving recess 308 can be open in a proximal direction, such that a rod R2 can be inserted into the recess by moving the rod distally with respect to the connector 300. Alternatively, the second rod-receiving recess 308 can be open in distal direction, open in a lateral direction, or closed such that the rod R2 must be translated along the axis A5 to insert the rod into the recess 308.

Each of the arms 334, 336 can include features 338 for retaining the saddle 322 within the body 306, e.g., of the type described above with respect to the connector 100. The second body 306 can include an outer bearing surface 340 configured to contact and bear against the outer bearing surface 330 of the first body 302. The distal end 306d of the second body 306 can define an interior cavity 342 in which a free end of the hinge pin 310 can be received. The cavity 342 can be open to the bearing surface 340 of the second body 306 and open to the second rod recess 308 as shown. In some embodiments, the cavity 342 can be a blind bore formed in the bearing surface 340 of the body 306 and intersecting with the second rod recess 308. At least one dimension of the cavity 342 can be greater than a corresponding dimension of the hinge pin 310 to allow the hinge pin to translate within the cavity along the rotation axis A1.

The bodies 302, 306 of the connector 300 can include various features for decreasing or increasing the center-to-center offset between the first and second rods R1, R2 when the rods are locked to the connector. For example, one or both of the outer surfaces of the bodies 302, 306 that oppose one another can be obliquely angled with respect to the respective proximal-distal axes A2, A4. Accordingly, the rods R1, R2 can move towards one another as they are advanced into the connector 300. This can advantageously reduce the center-to-center offset of the rods R1, R2, while preserving sufficient material thickness at the proximal ends of the bodies 302, 306 to withstand the relatively high forces subjected to the connector 300 during rod reduction, fastener tightening, and/or post-operative patient movement.

As another example, the opposing outer surfaces of the bodies 302, 306 can be parallel to the proximal-distal axes A2, A4, and instead the rod recesses 304, 308 can be obliquely angled or can follow a curved path with respect to the proximal-distal axes to bring the rods R1, R2 closer together.

As another example, the axis along which the first fastener 312 advances as it is tightened can be offset laterally from the first rod axis A3 when the first rod R1 is fully seated in the recess 304, or can be obliquely angled with respect to the proximal-distal axis A2 of the first body 302. Alternatively, or in addition, the axis along which the second fastener 314 advances as it is tightened can be offset laterally from the second rod axis A5 when the second rod R2 is fully seated in the recess 308, or can be obliquely angled with respect to the proximal-distal axis A4 of the second body 306.

The rotation axis A1 of the connector 300 can be perpendicular to the rod axis A3 and perpendicular to the rod axis A5. The rotation axis A1 can be perpendicular to the proximal-distal axis A2 of the first body, or can be obliquely angled with respect to the axis A2. The rotation axis A1 can be perpendicular to the proximal-distal axis A4 of the second body, or can be obliquely angled with respect to the axis A4. The proximal-distal axes A2, A4 of the bodies 302, 306 can be parallel to one another or can extend at an oblique angle with respect to one another.

The saddle 322 is shown in greater detail in FIGS. 3C, 3D, 3E, and 3F. The saddle 322 can be positioned within the body 306. The saddle 322 can be configured to translate within the body 306 along the axis A4, e.g., between proximal and distal limits defined by the interaction between the recesses 338 of the body 306 and projections 356 formed on the saddle.

The saddle 322 can be generally cylindrical with first and second arms 358, 360 extending in a proximal direction to respective free ends of the arms. The first and second arms 358, 360 can be aligned with the first and second arms 334, 336 of the body 306 such that a recess defined therebetween is aligned with the second rod-receiving recess 308. Accordingly, the second rod R2 can be simultaneously cradled between the arms 358, 360 of the saddle 322 and the arms 334, 336 of the body 306 when the rod is disposed in the second rod-receiving recess 308. The first and second arms 358, 360 of the saddle 322 can include projections 356 extending radially outward therefrom and configured to be received within the recesses 338 of the second body 306.

The distal-facing surface of the saddle 322 can define a recess 362 configured to receive at least a portion of the hinge pin 310. In the illustrated embodiment, the recess 362 is semi-cylindrical. The depth of the recess 362 can increase along the length of the recess to account for a body geometry in which the proximal-distal axis A4 of the body 306 is obliquely angled with respect to the rotation axis A1 of the hinge pin 310.

The saddle 322 can include one or more ramped, curved, or otherwise tapered surfaces configured to contact and bear against a counterpart surface of the hinge pin 310. For example, a keel projection 380 extending distally from the recess 362 of the saddle 322 can define a first bearing surface 366. The first bearing surface 366 can be planar. The first bearing surface 366 can lie in a plane that is obliquely angled with respect to the rotation axis A1. As shown in FIG. 3F, the first bearing surface 366 can include first and second planar portions that are obliquely angled relative to one another and relative to the axis A1, and that meet at a central ridge. This can facilitate smoother ramping when the connector bodies 302, 306 are rotated relative to one another from a neutral position.

The first fastener 312 can include an exterior thread configured to mate with the interior threads formed on the arms 324, 326 of the body 302 to allow the first fastener to be advanced or retracted along the axis A2 with respect to the body by rotating the first fastener about the axis A2. The first fastener 312 can include a driving interface 368 configured to receive a driver for applying a rotational force to the first fastener about the axis A2. The distal surface of the first fastener 312 can be configured to contact and bear against a rod R1 disposed in the first rod-receiving 304 recess to lock the rod to the connector 300. When tightened against the rod R1, the first fastener 312 can prevent the rod from translating relative to the connector 300 along the axis A3 and/or from rotating with respect to the connector about the axis A3. While a unitary set screw 312 is shown, it will be appreciated that other fasteners can be used instead or addition, such as a closure cap that advances and locks by quarter-turn rotation, a closure cap that slides in laterally without rotating, or a nut that threads onto an exterior of the body.

The second fastener 314 can include an exterior thread configured to mate with the interior threads formed on the arms 334, 336 of the second body 306 to allow the second fastener to be advanced or retracted along the axis A4 with respect to the body by rotating the second fastener about the axis A4. The second fastener 314 can include a driving interface 370 configured to receive a driver for applying a rotational force to the second fastener 314 about the axis A4. The distal surface of the second fastener 314 can be configured to contact and bear against a rod R2 disposed in the second rod-receiving 308 recess to lock the rod to the connector 300. When tightened against the rod R2, the second fastener 314 can prevent the rod from translating relative to the connector 300 along the axis A5 and/or from rotating with respect to the connector about the axis A5. While a unitary set screw 314 is shown, it will be appreciated that other fasteners can be used instead or addition, such as a closure cap that advances and locks by quarter-turn rotation, a closure cap that slides in laterally without rotating, a nut that threads onto an exterior of the body, or a dual-component set screw with independently-rotatable inner and outer members, the inner member acting on the rod R2 and the outer member acting on the saddle 322.

The hinge pin 310 can include opposed first and second ends that define a central longitudinal axis A6 extending therebetween. The longitudinal axis A6 can be collinear with the rotation axis A1 of the connector 300. The hinge pin 310 can be formed integrally or monolithically with the first body 302 as shown, or can be fixedly attached thereto, e.g., by welding or other processes. A free end of the hinge pin 310 can be received within the second body 306. The portion of the hinge pin 310 received within the second body 306 can include a slot 382 formed therein in which the keel 380 of the saddle 322 can be received. One or more sidewalls of the slot 382 can be ramped, curved, or otherwise tapered and configured to contact and bear against a counterpart surface of the saddle 322 or, in embodiments in which the saddle 322 is omitted, against a counterpart surface of the second rod R2. The illustrated hinge pin 310 includes a ramped bearing surface 320 configured to contact and bear against the bearing surface 366 of the saddle 322 as the second fastener 314 is tightened. The bearing surface 320 can be planar. The bearing surface 320 can lie in a plane that is obliquely angled with respect to the rotation axis A1.

As the second fastener 314 is tightened, the saddle 322 can be urged distally to translate the keel 380 distally within the slot 382. As the keel 380 moves within the slot 382, the bearing surface 366 of the keel can be urged along the counterpart bearing surface 320 of the hinge pin 310, causing the hinge pin to translate laterally within the cavity 342 of the second body 306 along the axis A1, thereby pulling the first body 302 towards the second body to lock relative rotation therebetween.

The distal end of the keel 380 can be tapered or bulleted to facilitate insertion of the keel into the slot 382. Insertion of the keel 380 into the slot 382 of the hinge pin 310 can prevent the hinge pin from being removed from the second body 306, thereby retaining the first and second bodies 302, 306 to one another, even before one or both rods R1, R2 are locked to the connector 300. Interaction between the keel 380 and the slot 382 can also be effective to limit the range of articulation between the first and second bodies 302, 306. For example, the slot 382 can have a width in a direction perpendicular to the axis A1 and perpendicular to the axis A4 that is greater than a corresponding width of the keel 380. The degree to which the bodies 302, 306 can rotate relative to one another about the axis A1 can be limited by the difference between the width of the slot 382 and the width of the keel 380.

The connector 300 can be assembled by inserting the free end of the hinge pin 310 into the cavity 342 of the second body 306. The saddle 322 can be inserted into the proximal end of the second body 306 and advanced distally until the projections 356 of the saddle snap into the grooves 338 of the second body 306 to retain the saddle therein. At this stage of assembly, even before locking rods within the connector 300, the saddle 322 can interfere with the slot 382 of the hinge pin 310 to prevent the hinge pin from being removed from the second body 306.

A first rod R1 can be seated in the first rod recess 304 and secured to the connector 300 by tightening the first fastener 312. The second body 306 can remain free to rotate relative to the first body 302 about the axis A1 even after the first rod R1 is locked to the connector 300.

A second rod R2 can be seated in the second rod recess 308 and secured to the connector 300 by tightening the second fastener 314. As the second fastener 314 is tightened, the second rod R2 can be urged distally against the saddle 322, in turn urging the saddle distally against the hinge pin 310. As the saddle 322 is urged distally, the ramped surface 366 of the saddle bears against the ramped surface 320 of the slot 382 in the hinge pin 310, applying a force to the hinge pin that urges the hinge pin deeper into the cavity 342.

Before fully tightening one or both fasteners 312, 314, the bodies 302, 306 can be rotated relative to one another about the axis A1 as desired by the user. The fastener 314 can then be tightened to lock such relative rotation. In particular, the force applied to the hinge pin 310 by the saddle 322 when the fastener 314 is tightened can cause the bodies 302, 306 to translate relative to one another along the axis A1, urging the bearing surfaces 330, 340 of the bodies into engagement with each other. Friction, mechanical interlock, or other forces between the bearing surfaces 330, 340 can be effective to lock relative rotation of the bodies 302, 306 about the axis A1. It will be appreciated that the connector 300 can allow locking of the first rod R1 to the connector and locking of the rotational degree-of-freedom of the connector to be performed independently of one another.

While a single, centrally-mounted keel 380 is described above, it will be appreciated that other configurations are possible. For example, as shown in FIGS. 3I-3L, the saddle 322 can include first and second keels 380A, 380B spaced apart from one another in the width dimension of the saddle. As also shown, the slot of the hinge pin 310 can be replaced with first and second slots 382A, 382B that form a reduced-width portion or central rib 384 of the hinge pin configured to be received between the keels 380A, 380B of the saddle 322 when the connector 300 is assembled. Each keel 380A, 380B can include a ramped, curved, or otherwise tapered bearing surface that contacts and bears against a corresponding surface of the hinge pin 310 adjacent the central rib 384. The relative widths of the rib 384 and the space between the keels 380A, 380B can be selected to limit the degree to which the first body 302 can rotate relative to the second body 306 about the axis A1.

FIGS. 4A-4F illustrate an exemplary embodiment of a connector 400. As shown, the connector 400 can include a first body 402 that defines a first rod-receiving recess or channel 404 and a second body 406 that defines a second rod-receiving recess or channel 408. The first and second bodies 402, 406 can be connected to one another at least in part by a hinge pin 410. The hinge pin 410 can define a rotation axis A1 about which the first and second bodies 402, 406 can rotate relative to one another. The connector 400 can include first and second fasteners 412, 414 configured to secure respective first and second rods R1, R2 or other fixation elements to the connector 400.

At least one of the fasteners 412, 414 can further be configured to urge the first and second bodies 402, 406 towards one another and thereby lock relative rotation of the first and second bodies about the rotation axis A1. For example, the second fastener 414 can be tightened to secure a second rod R2 within the second body 406 and to apply a force to a ramped, curved, or otherwise tapered surface 420 of the hinge pin 410 to draw the first and second bodies 402, 406 towards one another, locking rotation therebetween. In the illustrated embodiment, a force applied by the second fastener 414 is transferred to the hinge pin 410 through the second rod R2. The first fastener 412 can be tightened to secure a first rod R1 within the first body 402. The first fastener 412 can bear directly against the first rod R1 as shown, or against an intermediate rod pusher of the type described above with respect to the connector 200.

Except as indicated below and as will be readily appreciated by one having ordinary skill in the art in view of the present disclosure, the structure and operation of the connector 400 is the same as the connector 300 described above, and therefore a detailed description is omitted here for the sake of brevity.

As shown, the connector 400 can omit a saddle component, such that the second rod R2 bears directly against a rod seat 420 formed in the hinge pin 410. The rod seat 420 can be ramped, curved, or otherwise tapered. The rod seat 420 can have a width parallel to the axis A1 that is greater than the diameter of the second rod R2 and/or greater than the width of the second rod-receiving recess 408. The rod seat 420 can be located along the length of the hinge pin 410 at a position in which a lateral sidewall of the rod seat interferes with a rod R2 as the rod is seated in the second rod-receiving recess 408. As the rod R2 is advanced into the second rod-receiving recess 408, it can bear against the lateral sidewall of the rod seat 420 to cause the hinge pin 410 to translate along the axis A1, pulling the second body 406 towards the first body 402 to lock relative rotation therebetween.

Figure 4A:
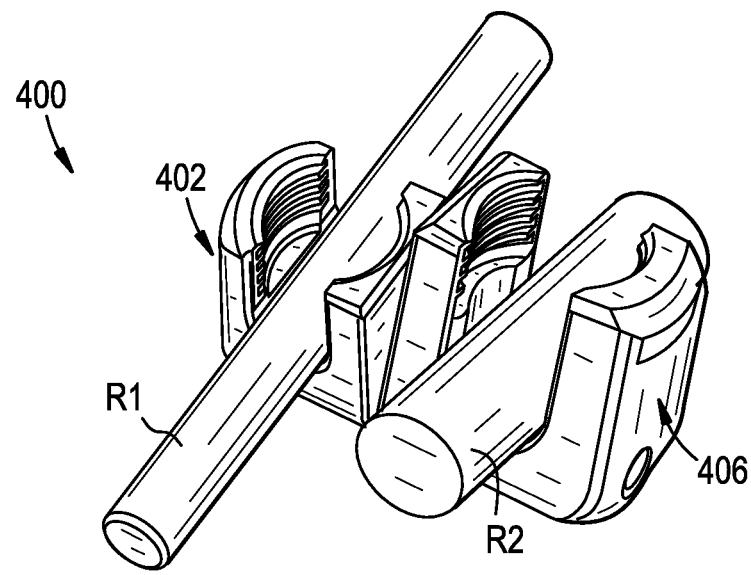
FIG. 4A is a perspective view of a connector, shown with first and second rods and with first and second fasteners of the connector omitted.
Figure 4B:
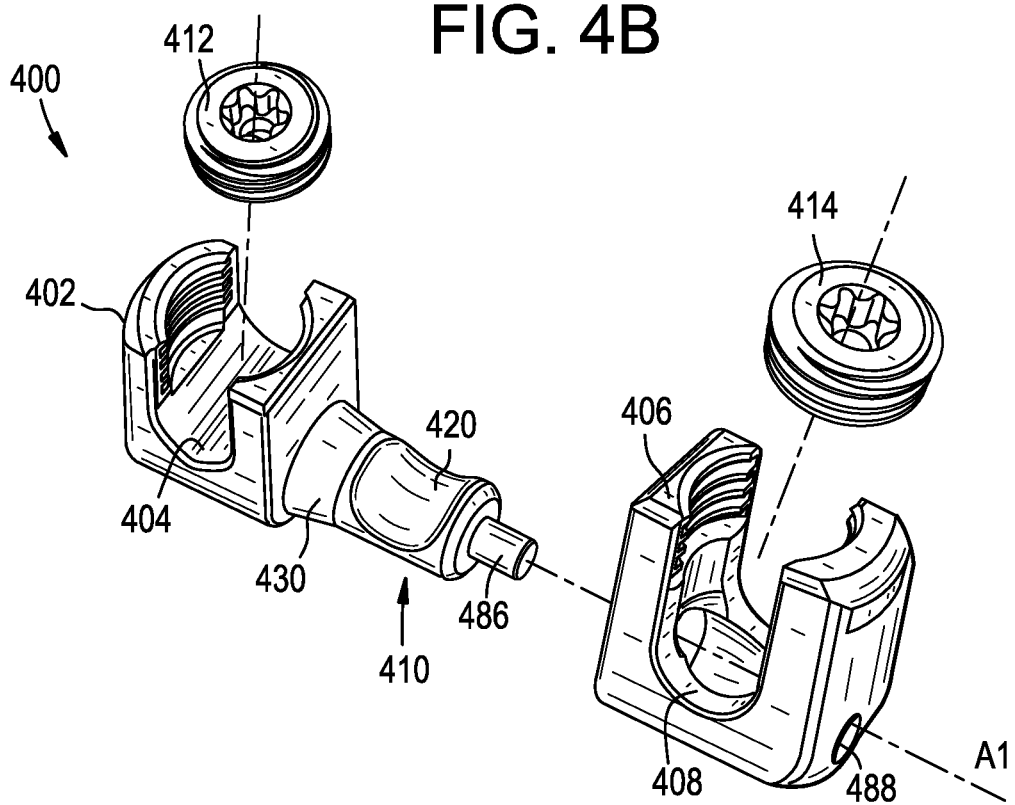
FIG. 4B is an exploded perspective view of the connector of FIG. 4A.
Figure 4C:
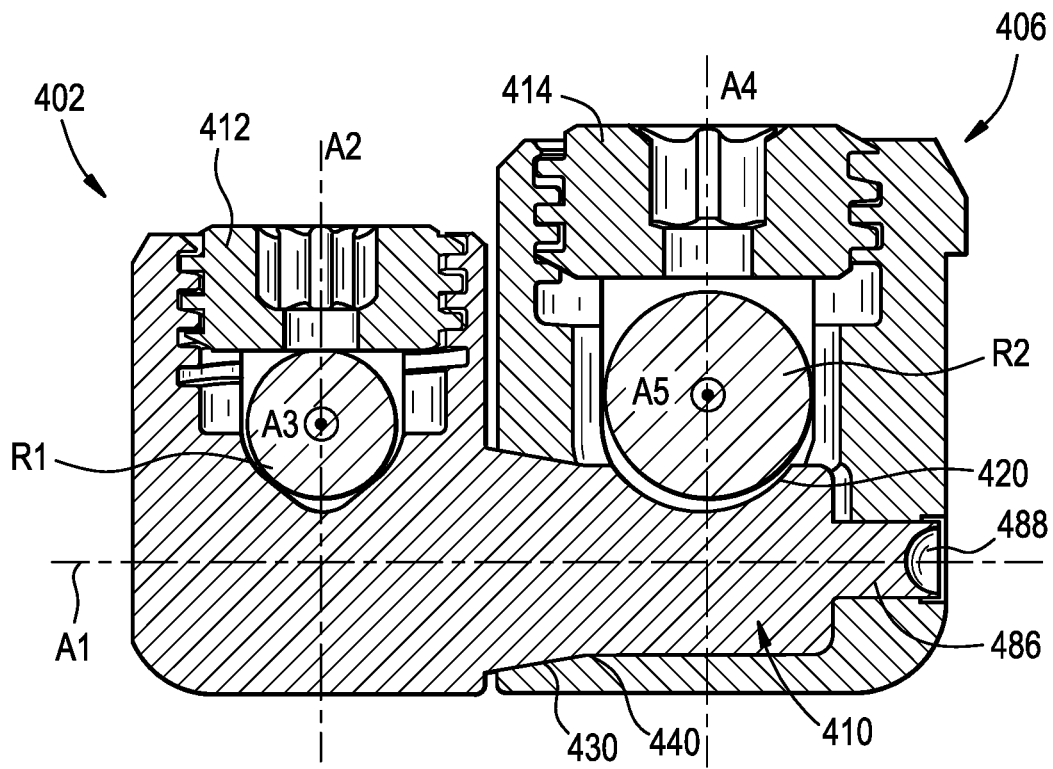
FIG. 4C is a sectional side view of the connector of FIG. 4A.
Figure 4D:
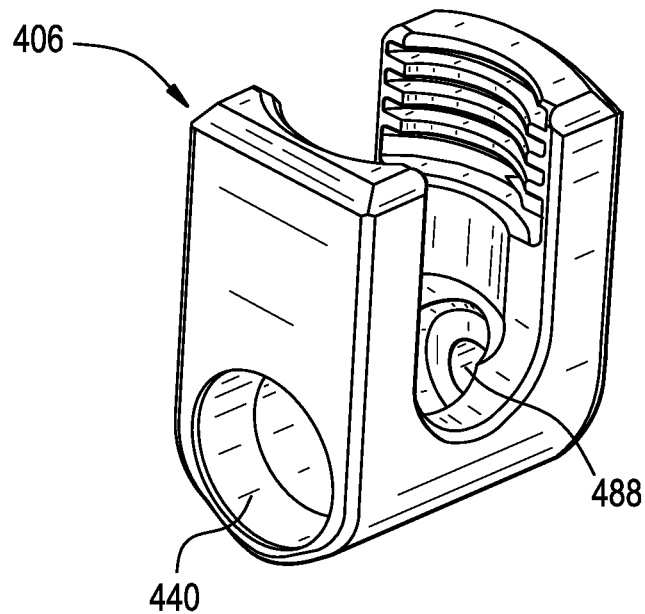
FIG. 4D is a perspective view of a second body of the connector of FIG. 4A.
Figure 4E:
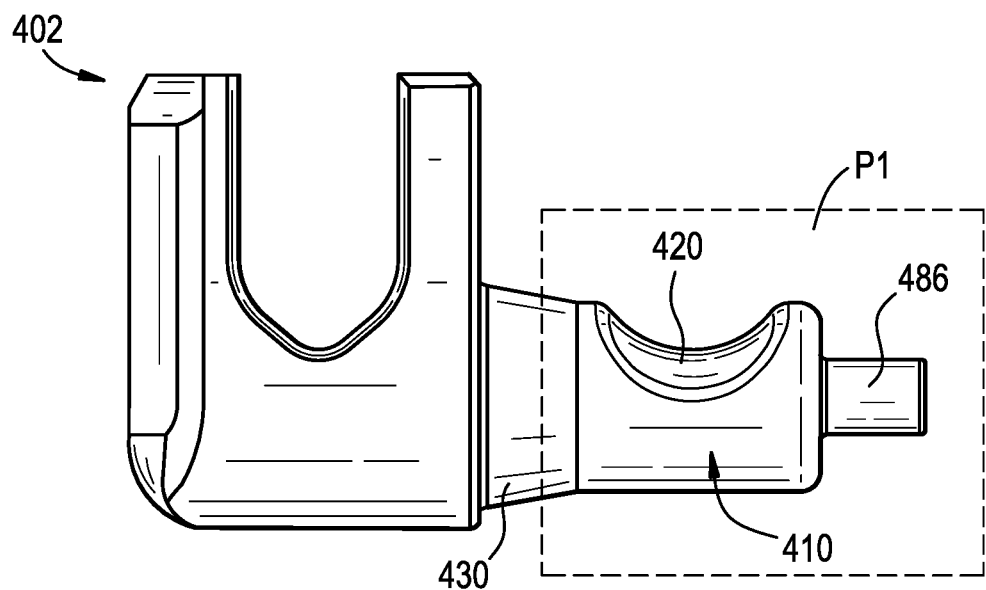
FIG. 4E is a side view of a first body of the connector of FIG. 4A.
Figure 4F:
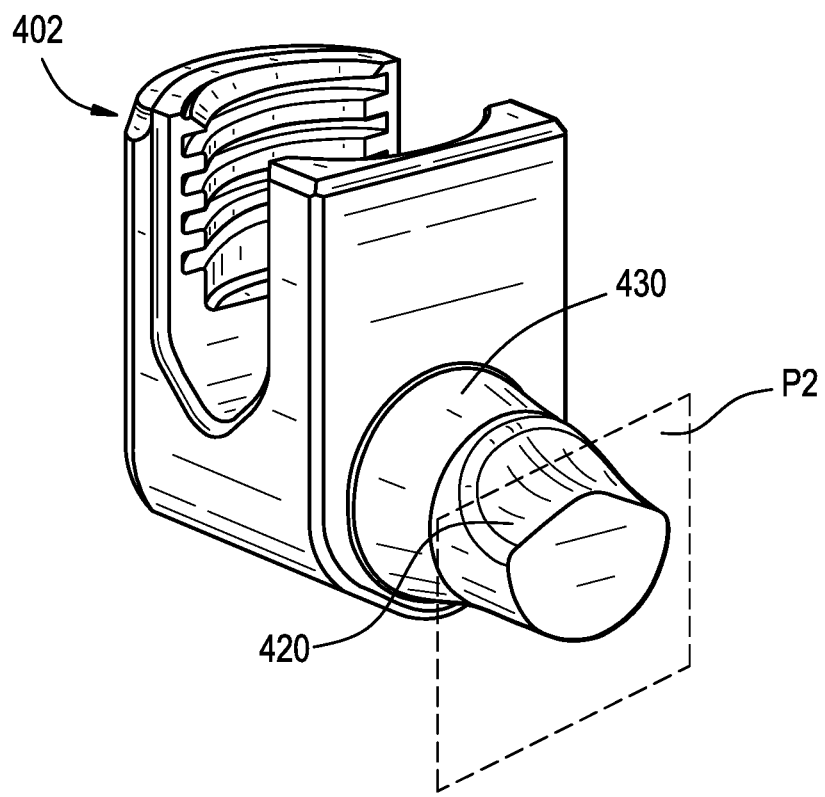
FIG. 4F is a perspective sectional view of the first body of the connector of FIG. 4A.

The rod seat 420 can be curved in multiple planes to allow the above-described bearing action to occur at any of a plurality of relative rotational positions about the axis A1 of the hinge pin 410 and the second body 406. For example, the rod seat 420 can be curved in a first plane defined by the axes A1, A2 and in a second plane defined by the axes A2, A3. As shown in FIG. 4E, the rod seat can have a circular cross section in a first plane P1. As shown in FIG. 4F, the rod seat 420 can have a cross section in a plane P2 perpendicular to the first plane P1 that is defined by first and second straight segments angled relative to one another and joined by an arcuate segment.

The rod seat 420 can be configured such that approximately the same ramp geometry is presented to the rod R2, regardless of the articulation angle of the first and second bodies 402, 406. The degree of curvature of the rod seat 420 in the second plane P2 can be configured to limit articulation of the first and second bodies 402, 406.

The hinge pin 410 can be retained within the second body 406 using various techniques, such as swaging or a retention pin that limits axial translation of the hinge pin relative to the body while still permitting rotation of the hinge pin relative to the second body. In the illustrated embodiment, the free end of the hinge pin 410 includes a post or rivet tail 486 that projects axially therefrom. The post 486 can be received within a through-hole 488 formed in the second body 406 and thereafter swaged, deformed, flattened, or otherwise modified such that the post cannot be freely removed from the through-hole. The terminal end of the post 486 can be cupped or hollowed to facilitate deformation of the post during the swaging process.

Any of the connectors 100, 200, 300, 400 described above can include a taper-lock mating between the first and second bodies. The taper lock can be formed by a conical male feature wedged into a conical female feature. The cone angle of the male feature can be in the range of about 5 degrees to about 35 degrees. The cone angle of the male feature can be about 20 degrees. The cone angle of the female feature can be in the range of about 5 degrees to about 35 degrees. The cone angle of the female feature can be about 20 degrees. The male and female cone features can have the same cone angle or different cone angles. The connector geometry can be selected such that there is a space between the first and second bodies along the axis A1 when the connector is fully tightened, which can ensure that the taper lock bears most or all of the locking force. The male and female features can be flat cones, or can include surface features such as axial splines.

The degree to which the first and second bodies can rotate relative to one another can vary in any of the connectors 100, 200, 300, 400 described above. The first body can be rotatable up to 360 degrees with respect to the second body. The first body can be rotatable up to about 180 degrees with respect to the second body. The first body can be rotatable up to about 60 degrees with respect to the second body.

The geometries of the rod-receiving recesses of any of the connectors 100, 200, 300, 400 described above can vary. One or both recesses can include a V-shaped seat configured to accommodate rods of different diameters.

An exemplary method of using the connectors disclosed herein is described below.

Figure 5:
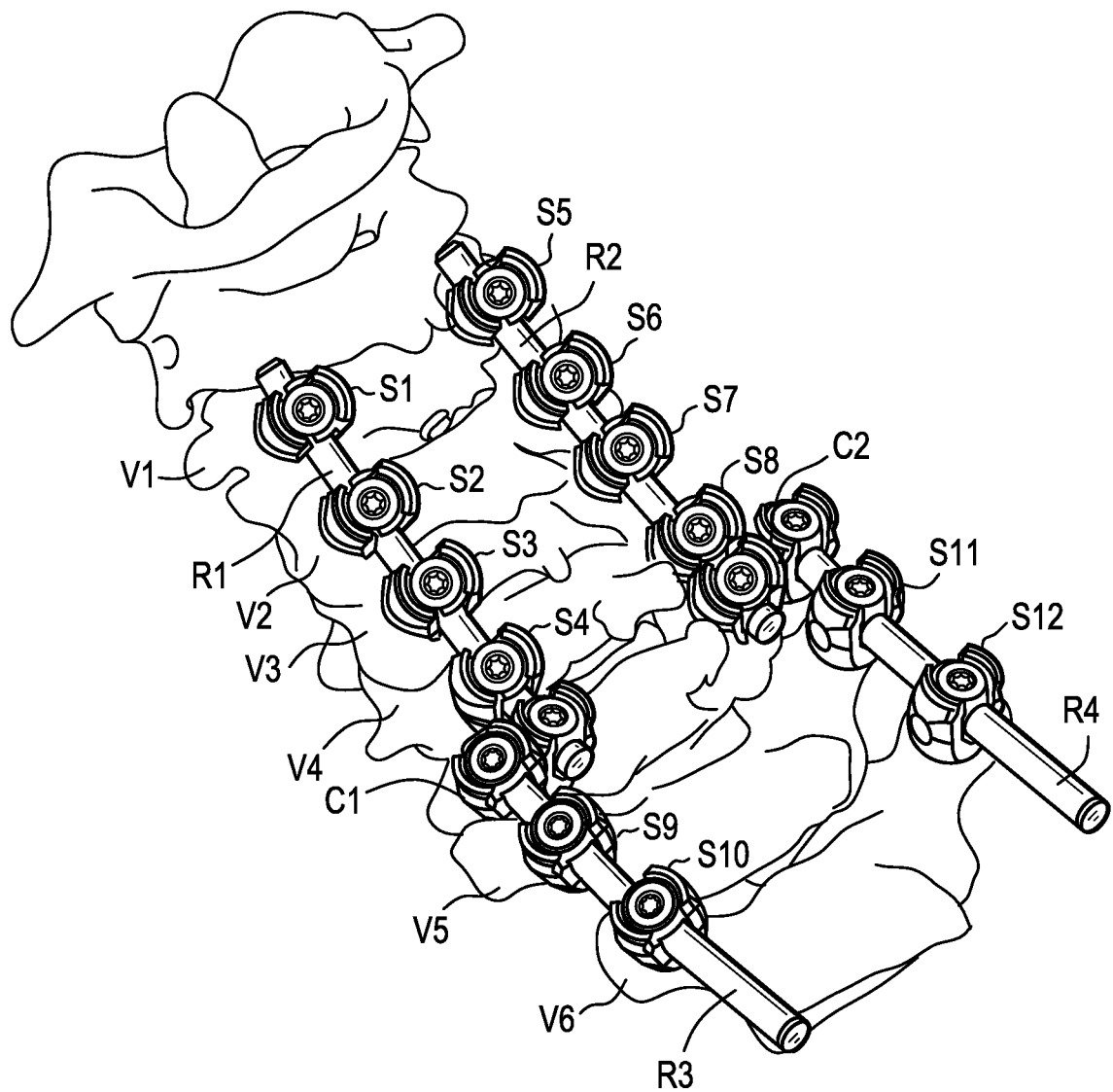
FIG. 5 is a perspective view of a human spine with a fixation system attached thereto.

The procedure can begin by forming an open or percutaneous incision in the patient to access a target site. The target site can be one or more vertebrae, a long bone or multiple portions of a long bone, or any other bone or non-bone structure of the patient. As shown in FIG. 5, the target site can be multiple vertebrae in the patient's cervical and thoracic spine.

Bone anchors can be driven into one or more of the vertebrae and spinal rods can be attached thereto using known techniques. In the illustrated example, bilateral spinal rods R1, R2 are coupled to four adjacent vertebrae V1-V4 using eight bone anchors S1-S8. In addition, bilateral rods R3, R4 are coupled to two additional vertebrae V5-V6 using four bone anchors S9-S12. The rods R1, R2 can be connected to the rods R3, R4, respectively, using two connectors C1-C2 of the type described herein (e.g., any of the connectors 100, 200, 300, 400 or combinations or variations thereof).

The connectors C1-C2 can be articulated and locked in an articulated position as shown. This can allow the principal longitudinal axes of the rods R1, R3 to be obliquely angled with respect to each other, and/or for the principal longitudinal axes of the rods R2, R4 to be obliquely angled with respect to each other.

All of the rods R1-R4, the connectors C1-C2, and the bone anchors S1-S12 can be installed in a single procedure.

Alternatively, the rods R1, R2 and the bone anchors S1-S8 may have been installed in a previous procedure, and the current procedure can be a revision procedure in which the rods R3, R4, the connectors C1-C2, and the bone anchors S9-S12 are installed to extend the previously-installed construct to additional levels.

The connectors C1-C2 can be attached to position the rods R1-R4 such that they overlap in a lateral view. One or both connectors C1-C2 can also be rotated 90 degrees from the orientation shown to position one or both rod pairs R1, R3 and R2, R4 such that they overlap in a posterior or anterior view.

The above steps can be repeated to install additional rods and/or connectors at the same or at different vertebral levels. Final tightening or other adjustment of the construct can be performed and the procedure can be completed using known techniques and the incision closed.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

While the methods illustrated and described herein generally involve attaching spinal rods to multiple vertebrae, it will be appreciated that the connectors and methods herein can be used with various other types of fixation or stabilization hardware, in any bone, in non-bone tissue, or in non-living or non-tissue objects. The connectors disclosed herein can be fully implanted, or can be used as part of an external fixation or stabilization system. The devices and methods disclosed herein can be used in minimally-invasive surgery and/or open surgery.

The devices disclosed herein and the various component parts thereof can be constructed from any of a variety of known materials. Exemplary materials include those which are suitable for use in surgical applications, including metals such as stainless steel, titanium, or alloys thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

Although specific embodiments are described above, it should be understood that numerous changes may be made within the spirit and scope of the concepts described.

The invention claimed is:

1. A connector, comprising:
a first body that defines a pair of spaced apart arms that define a first rod-receiving recess therebetween, the first body having a proximal end and a distal end that define a first proximal-distal axis extending therebetween, the first rod-receiving recess having a rod-receiving opening formed in the proximal end of the first body;
a second body that defines a second rod-receiving recess, the second body having a proximal end and a distal end that define a second proximal-distal axis extending therebetween, the second rod-receiving recess having a rod-receiving opening formed in the proximal end of the second body;
a hinge pin that is one of integrally formed with the first body or fixedly attached to an outer surface of the first body that couples the first body to the second body, the hinge pin extending laterally from the first body to a free end with a central longitudinal axis about which the first and second bodies rotate relative to one another;
a first fastener movable from the proximal end of the first body towards the distal end of the first body to secure a rod received within the first rod-receiving recess; and
a second fastener movable with respect to the second body to urge the first and second bodies towards one another along the central longitudinal axis and thereby lock relative rotation of the first and second bodies about the central longitudinal axis.

2. The connector of claim 1, wherein the central longitudinal axis of the hinge pin is transverse to the first and second proximal-distal axes.

3. The connector of claim 1, wherein the first proximal-distal axis is perpendicular to the central longitudinal axis of the hinge pin.

4. The connector of claim 1, wherein the first proximal-distal axis and the second proximal-distal axis are parallel to one another.

5. The connector of claim 1, wherein the first proximal-distal axis and the second proximal-distal axis extend at oblique angles relative to one another.

6. The connector of claim 1, wherein the second fastener is movable relative to the second rod-receiving recess to secure a rod received within the second rod-receiving recess.

7. The connector of claim 1, wherein the free end of the hinge pin is received within a cavity formed in the second body.

8. The connector of claim 1, wherein a force applied by the second fastener is transferred to the hinge pin through a saddle.

9. The connector of claim 8, wherein the hinge pin includes a slot formed therein and the saddle includes a distally extending keel received within the slot of the hinge pin.

10. The connector of claim 9, wherein the keel has a bearing surface that engages and bears against a corresponding bearing surface of the slot to pull the first and second bodies towards one another.

11. The connector of claim 10, wherein the bearing surfaces of the keel and the slot lie in planes that are obliquely angled with respect to the central longitudinal axis.

12. The connector of claim 8, wherein the saddle includes first and second keels defining a space therebetween in which a central rib of the hinge pin is received, the first and second keels having bearing surfaces that engage and bear against corresponding bearing surfaces of the hinge pin.

13. The connector of claim 1, wherein the free end of the hinge pin terminates within the second rod-receiving recess.

14. The connector of claim 1, wherein the first rod-receiving recess is open in a proximal direction to allow a rod to be inserted into the first rod-receiving recess by moving the rod distally into the rod-receiving opening of the first body.

15. A connector, comprising:
a first body that defines a first rod-receiving recess between a first pair of spaced apart arms, the first body having a proximal end and a distal end that define a first proximal-distal axis extending therebetween and a first bearing surface, wherein the first rod-receiving recess is configured to receive a first rod along the first proximal-distal axis;
a second body that defines a second rod-receiving recess between a second pair of spaced apart arms, the second body having a proximal end and a distal end that define a second proximal-distal axis extending therebetween and a second bearing surface configured to contact and bear against the first bearing surface of the first body, wherein the second rod-receiving recess is configured to receive a second rod along the second-proximal distal axis;
a hinge pin extending laterally from the first body to a free end with a central longitudinal axis about which the first and second bodies rotate relative to one another, the hinge pin being one of integrally formed with the first body or fixedly attached to an outer surface of the first body; and a fastener received within the second body to urge the first and second bodies towards one another along the central longitudinal axis and thereby lock relative rotation of the first and second bodies about the central longitudinal axis, wherein the free end of the hinge pin is received within a cavity formed in the second body to couple the second body to the first body.

16. The connector of claim 15, wherein the cavity formed in the second body intersects the second rod-receiving recess.

17. The connector of claim 15, wherein the cavity is a blind bore formed in the second body.

18. The connector of claim 15, wherein the first bearing surface and the second bearing surface bear against one another to lock relative rotation between the first body and second body as the first body and the second body are urged towards one another.

19. The connector of claim 15, wherein the first bearing surface is an exterior surface of the hinge pin.

20. The connector of claim 19, wherein the first bearing surface is a projection and the second bearing surface is a surface of an opening in the second body configured to receive the projection.

21. The connector of claim 15, wherein at least one dimension of the cavity is greater than a corresponding dimension of the hinge pin such that the hinge pin can translate within the cavity along the central longitudinal axis.

22. The connector of claim 15, wherein the second body includes a first arm extending proximally from the distal end of the second body and a second arm extending proximally from the distal end of the second body with the second rod-receiving recess formed therebetween, and wherein the cavity extends through one of the first and second arms without extending through the other of the first and second arms.

23. The connector of claim 15, wherein the first proximal-distal axis and the second proximal-distal axis do not intersect.

24. The connector of claim 15, wherein the first proximal-distal axis and the second proximal-distal axis are perpendicular to the central longitudinal axis.

25. A connector, comprising:

a first body that defines a first rod-receiving recess, the first body having a proximal end and a distal end that define a first proximal-distal axis extending therebetween;

a hinge pin extending laterally from the first body to a free end with a central longitudinal axis that is substantially transverse to the first proximal-distal axis, the hinge pin being one of integrally formed with the first body or fixedly attached to an outer surface of the first body with a slot formed therein;

a second body that defines a second rod-receiving recess, the second body having a proximal end and a distal end that define a second proximal-distal axis extending therebetween, the second body having a cavity that is configured to receive the hinge pin therethrough to couple the first body to the second body;

a saddle received in the second rod-receiving recess, the saddle having one or more distally-extending projections that define a first bearing surface;

wherein the hinge pin includes a slot that aligns with the second proximal-distal axis when the first body is coupled to the second body, the slot being configured to receive the one or more distally-extending projections such that the first bearing surface is configured to contact and bear against a second bearing surface of the hinge pin to cause the hinge pin to translate laterally within the cavity of the second body along the central longitudinal axis to lock relative rotation between the first body and the second body.

* * * * *